US011862313B2

(12) United States Patent
Ponceleon et al.

(10) Patent No.: US 11,862,313 B2
(45) Date of Patent: *Jan. 2, 2024

(54) DECENTRALIZED PRESCRIPTION REFILLS

(71) Applicant: International Business Machines Corporation, Armonk, NY (US)

(72) Inventors: Dulce B. Ponceleon, Palo Alto, CA (US); Nathalie Baracaldo Angel, San Jose, CA (US); Nitin Gaur, Roundrock, TX (US)

(73) Assignee: International Business Machines Corporation, Armonk, NY (US)

( * ) Notice: Subject to any disclaimer, the term of this patent is extended or adjusted under 35 U.S.C. 154(b) by 620 days.

This patent is subject to a terminal disclaimer.

(21) Appl. No.: 16/436,904

(22) Filed: Jun. 10, 2019

(65) Prior Publication Data

US 2020/0388366 A1    Dec. 10, 2020

(51) Int. Cl.
*G16H 20/10* (2018.01)
*G16H 10/60* (2018.01)
(Continued)

(52) U.S. Cl.
CPC ......... *G16H 20/10* (2018.01); *G06F 16/2365* (2019.01); *G06F 16/2379* (2019.01);
(Continued)

(58) Field of Classification Search
CPC .. G06F 16/27; G06F 16/2379; G06F 16/2365; G06F 21/602; H04L 2209/38; G16B 50/00
See application file for complete search history.

(56) References Cited

U.S. PATENT DOCUMENTS 7,072,840 B1    7/2006    Mayaud
2003/0050802 A1    3/2003    Jay et al.
(Continued)

FOREIGN PATENT DOCUMENTS

CN    107835182 A    3/2018
WO    WO2018064645 A1 *    9/2017    ............... G06K 5/02
(Continued)

OTHER PUBLICATIONS

Zhang, P. (2018). Architectures and patterns for moving towards the use of high-frequency, low-fidelity data in healthcare (Order No. 13877345). Available from ProQuest Dissertations and Theses Professional. (2211212667). (Year: 2018).*

(Continued)

*Primary Examiner* — Jason S Tiedeman
*Assistant Examiner* — Emily Huynh

(57) ABSTRACT

An example operation may include one or more of connecting, by a pharmacy node, to a blockchain network configured to store patients' data on a blockchain ledger, receiving, by the pharmacy node, a request from a patient node for a prescription refill, the request contains a secret key of a patient, extracting, by the pharmacy node, the secret key from the request to verify a patient's identity, and executing, by the pharmacy node, a smart contract to: (a) decrypt a prescription data located on the ledger by an application of the secret key, (b) retrieve patient's allergy records from the ledger to check the allergy records against the prescription data, (c) determine a number of remaining refills from the prescription data, (d) check validity of the prescription data based on an expiration date, and commit a prescription refill transaction to the blockchain based on a successful execution of (b)-(d).

14 Claims, 13 Drawing Sheets

(51) Int. Cl.
    *G06F 16/27* (2019.01)
    *G06F 21/60* (2013.01)
    *G06F 16/23* (2019.01)
    *H04L 9/06* (2006.01)
    *H04L 9/00* (2022.01)

(52) U.S. Cl.
    CPC ............ *G06F 16/27* (2019.01); *G06F 21/602* (2013.01); *G16H 10/60* (2018.01); *H04L 9/0637* (2013.01); *H04L 9/50* (2022.05)

(56) References Cited

U.S. PATENT DOCUMENTS

| | | | |
|---|---|---|---|
| 2005/0041531 A1* | 2/2005 | Sekura | A61J 7/04 368/10 |
| 2009/0164376 A1 | 6/2009 | Guthrie | |
| 2010/0169218 A1 | 7/2010 | Wang et al. | |
| 2012/0150562 A1* | 6/2012 | Lerner | G16H 10/60 705/3 |
| 2013/0191139 A1 | 7/2013 | Chen et al. | |
| 2015/0261934 A1 | 9/2015 | Miller | |
| 2016/0012203 A1 | 1/2016 | Huser | |
| 2016/0117471 A1 | 4/2016 | Belt et al. | |
| 2017/0132393 A1 | 5/2017 | Natarajan et al. | |
| 2017/0169186 A1* | 6/2017 | Tumma | G16H 20/10 |
| 2017/0300627 A1 | 10/2017 | Giordano et al. | |
| 2018/0121620 A1 | 5/2018 | Bastide et al. | |
| 2018/0165416 A1 | 6/2018 | Saxena et al. | |
| 2018/0253464 A1 | 9/2018 | Kohli et al. | |
| 2019/0057763 A1* | 2/2019 | Stockert | G16H 10/00 |
| 2019/0156938 A1* | 5/2019 | Brunner | H04L 9/0643 |
| 2019/0198144 A1 | 6/2019 | Blackley et al. | |
| 2019/0206536 A1 | 7/2019 | Hausman | |
| 2019/0237176 A1 | 8/2019 | O'Brien et al. | |
| 2019/0237178 A1 | 8/2019 | Shaye | |
| 2020/0388366 A1 | 12/2020 | Ponceleon et al. | |
| 2021/0065864 A1 | 3/2021 | Lamoncha | |

FOREIGN PATENT DOCUMENTS

| | | | | |
|---|---|---|---|---|
| WO | 2018037148 A1 | 3/2018 | | |
| WO | 2018197739 A1 | 11/2018 | | |
| WO | WO-2018197739 A1 * | 11/2018 | ........... | H04L 9/3236 |

OTHER PUBLICATIONS

List of IBM Patents or Patent Applications Treated as Related, Jun. 15, 2019.

Dulce B. Ponceleon et al., "Decentralized Prescription Refills", U.S. Appl. No. 16/436,893, filed Jun. 10, 2019.

* cited by examiner

700

DECENTRALIZED PRESCRIPTION REFILLS

TECHNICAL FIELD

This application generally relates to a database storage system, and more particularly, to decentralized prescription refills.

BACKGROUND

A centralized database stores and maintains data in one single database (e.g., database server) at one location. This location is often a central computer, for example, a desktop central processing unit (CPU), a server CPU, or a mainframe computer. Information stored on a centralized database is typically accessible from multiple different points. Multiple users or client workstations can work simultaneously on the centralized database, for example, based on a client/server configuration. A centralized database is easy to manage, maintain, and control, especially for purposes of security because of its single location. Within a centralized database, data redundancy is minimized as a single storing place of all data also implies that a given set of data only has one primary record.

However, a centralized database suffers from significant drawbacks. For example, a centralized database has a single point of failure. In particular, if there are no fault-tolerance considerations and a hardware failure occur (for example, the hardware, a firmware, and/or a software failure), all data within the database is lost and work of all users is interrupted. In addition, centralized databases are highly dependent on network connectivity. As a result, the slower the connection, the amount of time needed for each database access is increased. Another drawback is the occurrence of bottlenecks when a centralized database experiences high traffic due to a single location. Furthermore, a centralized database provides limited access to data because only one copy of the data is maintained by the database. As a result, multiple devices cannot access the same piece of data at the same time without creating significant problems or risk overwriting stored data. Furthermore, because a database storage system has minimal to no data redundancy, data that is unexpectedly lost is very difficult to retrieve other than through manual operation from back-up storage.

Conventionally, a centralized database is limited by low search capability, lack of security and slow speed of transactions. As such, what is needed is a blockchain-based solution to overcome these significant drawbacks.

Obtaining medications while traveling abroad or in an unfamiliar location can be difficult and expensive. People traveling abroad sometimes forget to buy their medication for their upcoming travel or may run out of medications during their trip, or may lose their medications. People may rush before the trip and may end up paying more for their medication. In some cases, a person may even decide to travel without medications putting his or her health at risk. When medications are not available over the counter, it becomes expensive and time consuming to refill a prescription, because some medications may require a doctor's visit to obtain a prescription in a different country or at a location a patient is not familiar with. Moreover, while in some locations a particular medication may be available over-the-counter, in another location it may be restricted. For example, in Canada, Piralvex™ can be bought over the counter, while in the U.S. this medicine requires a prescription. Hence, even if a traveler has planned a trip carefully, he or she may still face problems trying to buy a medicine that they originally thought could be acquired over the counter. Even in case when the medication requires prescription in the home country, but can be acquired over-the-counter in the destination country, it is still desirable to have a system that notifies the traveler about the over-the-counter availability. It is important to ensure that people can obtain their medications on time without jeopardizing their health at a minimum cost and without hassles. For example, a person that requires insulin, asthma inhalers, albuterol or even birth-control pills, should be able to obtain their medications even when they are abroad without any problems.

Accordingly, it is desired to enable travelers to easily refill their prescriptions when they travel abroad or to an unfamiliar location using a blockchain as a way to securely process information related to medical insurance, medical conditions, allergies and to provide required identification mechanisms to prove the identity of a patient.

SUMMARY

One example embodiment provides a method that includes one or more of connecting, by a pharmacy node, to a blockchain network configured to store patients' data on a blockchain ledger, receiving, by the pharmacy node, a request from a patient node for a prescription refill, the request contains a secret key of a patient, extracting, by the pharmacy node, the secret key from the request to verify a patient's identity, and executing, by the pharmacy node, a smart contract to: (a) decrypt a prescription data located on the ledger by an application of the secret key, (b) retrieve patient's allergy records from the ledger to check the allergy records against the prescription data, (c) determine a number of remaining refills from the prescription data, (d) check validity of the prescription data based on an expiration date, and commit a prescription refill transaction to the blockchain based on a successful execution of (b)-(d).

A further example embodiment provides a non-transitory computer readable medium comprising instructions, that when read by a processor, cause the processor to perform one or more of connecting to a blockchain network configured to store patients' data on a blockchain ledger, receiving a request from a patient node for a prescription refill, the request contains a secret key of a patient, extracting the secret key from the request to verify a patient's identity, and executing a smart contract to (a) decrypt a prescription data located on the ledger by an application of the secret key, (b) retrieve patient's allergy records from the ledger to check the allergy records against the prescription data (c) determine a number of remaining refills from the prescription data, (d) check validity of the prescription data based on an expiration date, and commit a prescription refill transaction to the blockchain based on a successful execution of (b)-(d).

Another example embodiment provides a method that includes one or more of receiving, by a pharmacy node, a request from a patient node for a prescription refill, the request contains a secret key of a patient, extracting, by the pharmacy node, the secret key from the request to verify a patient's identity, and executing, by the pharmacy node, a smart contract to (a) decrypt a prescription data located on the ledger by an application of the secret key, (b) retrieve patient's allergy records from the ledger to check the allergy records against the prescription data, (c) determine a number of remaining refills from the prescription data, check validity of the prescription data based on an expiration date, and commit a prescription refill transaction to the blockchain based on a successful execution of (b)-(d).

DETAILED DESCRIPTION

Figure 1:
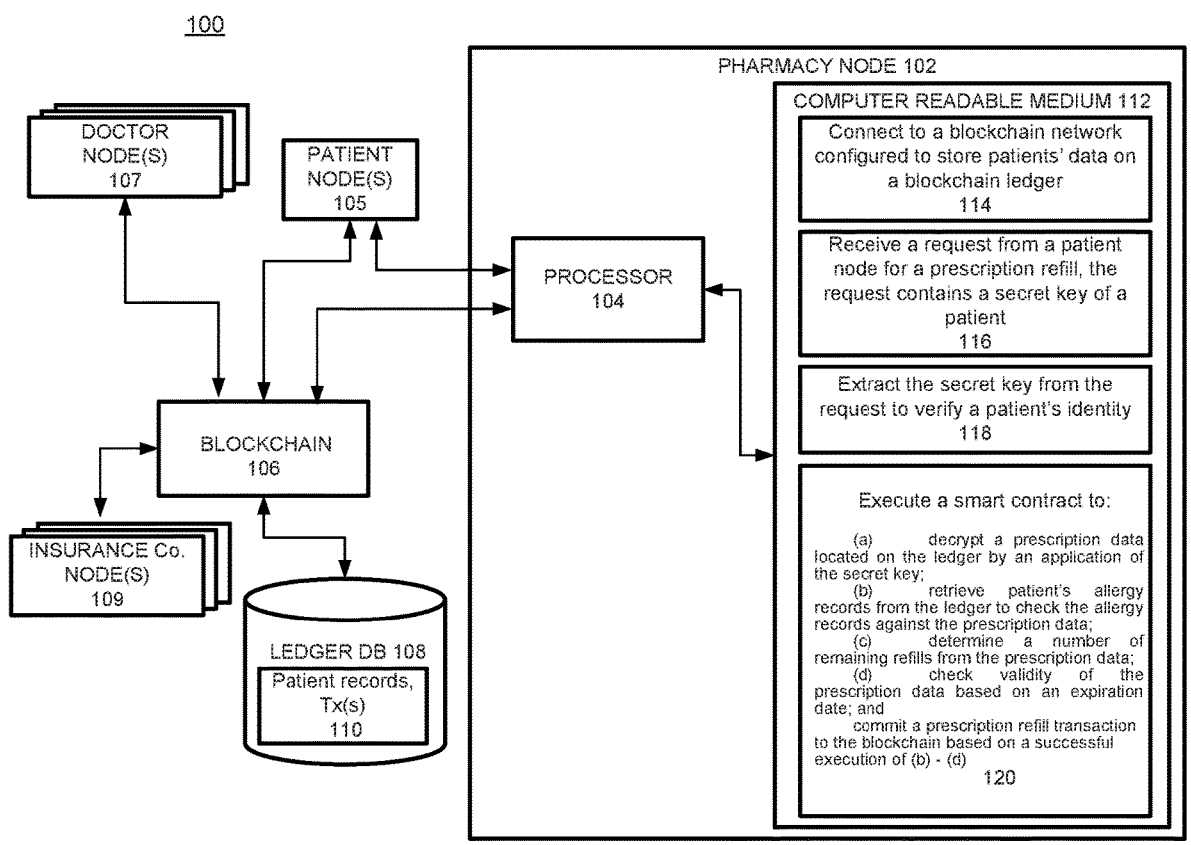
FIG. 1 illustrates a network diagram of a system including a ledger database, according to example embodiments.

It will be readily understood that the instant components, as generally described and illustrated in the figures herein, may be arranged and designed in a wide variety of different configurations. Thus, the following detailed description of the embodiments of at least one of a method, apparatus, non-transitory computer readable medium and system, as represented in the attached figures, is not intended to limit the scope of the application as claimed but is merely representative of selected embodiments.

The instant features, structures, or characteristics as described throughout this specification may be combined in any suitable manner in one or more embodiments. For example, the usage of the phrases "example embodiments", "some embodiments", or other similar language, throughout this specification refers to the fact that a particular feature, structure, or characteristic described in connection with the embodiment may be included in at least one embodiment. Thus, appearances of the phrases "example embodiments", "in some embodiments", "in other embodiments", or other similar language, throughout this specification do not necessarily all refer to the same group of embodiments, and the described features, structures, or characteristics may be combined in any suitable manner in one or more embodiments.

In addition, while the term "message" may have been used in the description of embodiments, the application may be applied to many types of network data, such as, packet, frame, datagram, etc. The term "message" also includes packet, frame, datagram, and any equivalents thereof. Furthermore, while certain types of messages and signaling may be depicted in exemplary embodiments they are not limited to a certain type of message, and the application is not limited to a certain type of signaling.

Example embodiments provide methods, systems, components, non-transitory computer readable media, devices, and/or networks, which provide for decentralized prescription refills over a blockchain network.

A decentralized database is a distributed storage system which includes multiple nodes that communicate with each other. A blockchain is an example of a decentralized database which includes an append-only immutable data structure resembling a distributed ledger capable of maintaining records between mutually untrusted parties. The untrusted parties are referred to herein as peers or peer nodes. Each peer maintains a copy of the database records and no single peer can modify the database records without a consensus being reached among the distributed peers. For example, the peers may execute a consensus protocol to validate blockchain storage transactions, group the storage transactions into blocks, and build a hash chain over the blocks. This process forms the ledger by ordering the storage transactions, as is necessary, for consistency. In a public or permission-less blockchain, anyone can participate without a specific identity. Public blockchains often involve native crypto-currency and use consensus based on various protocols such as Proof of Work (PoW). On the other hand, a permissioned blockchain database provides a system which can secure inter-actions among a group of entities which share a common goal, but which do not fully trust one another, such as businesses that exchange funds, goods, information, and the like.

A blockchain operates arbitrary, programmable logic, tailored to a decentralized storage scheme and referred to as "smart contracts" or "chaincodes." In some cases, specialized chaincodes may exist for management functions and parameters which are referred to as system chaincode. Smart contracts are trusted distributed applications which leverage tamper-proof properties of the blockchain database and an underlying agreement between nodes which is referred to as an endorsement or endorsement policy. In general, blockchain transactions typically must be "endorsed" before being committed to the blockchain while transactions which are not endorsed are disregarded. A typical endorsement policy allows chaincode to specify endorsers for a transaction in the form of a set of peer nodes that are necessary for endorsement. When a client sends the transaction to the peers specified in the endorsement policy, the transaction is executed to validate the transaction. After validation, the transactions enter an ordering phase in which a consensus protocol is used to produce an ordered sequence of endorsed transactions grouped into blocks.

Nodes are the communication entities of the blockchain system. A "node" may perform a logical function in the sense that multiple nodes of different types can run on the same physical server. Nodes are grouped in trust domains and are associated with logical entities that control them in various ways. Nodes may include different types, such as a client or submitting-client node which submits a transaction-invocation to an endorser (e.g., peer), and broadcasts transaction-proposals to an ordering service (e.g., ordering node). Another type of node is a peer node which can receive client submitted transactions, commit the transactions and maintain a state and a copy of the ledger of blockchain transactions. Peers can also have the role of an endorser, although it is not a requirement. An ordering-service-node or orderer is a node running the communication service for all nodes, and which implements a delivery guarantee, such as a broadcast to each of the peer nodes in the system when committing transactions and modifying a world state of the blockchain, which is another name for the initial blockchain transaction which normally includes control and setup information.

A ledger is a sequenced, tamper-resistant record of all state transitions of a blockchain. State transitions may result from chaincode invocations (i.e., transactions) submitted by participating parties (e.g., client nodes, ordering nodes, endorser nodes, peer nodes, etc.). A transaction may result in a set of asset key-value pairs being committed to the ledger as one or more operands, such as creates, updates, deletes, and the like. The ledger includes a blockchain (also referred to as a chain), which is used to store an immutable, sequenced record in blocks. The ledger also includes a state database which maintains a current state of the blockchain. There is typically one ledger per channel. Each peer node maintains a copy of the ledger for each channel of which they are a member.

A chain is a transaction log which is structured as hash-linked blocks, and each block contains a sequence of N transactions where N is equal to or greater than one. The block header includes a hash of the block's transactions, as well as a hash of the prior block's header. In this way, all transactions on the ledger may be sequenced and cryptographically linked together. Accordingly, it is not possible to tamper with the ledger data without breaking the hash links. A hash of a most recently added blockchain block represents every transaction on the chain that has come before it, making it possible to ensure that all peer nodes are in a consistent and trusted state. The chain may be stored on a peer node file system (i.e., local, attached storage, cloud, etc.), efficiently supporting the append-only nature of the blockchain workload.

The current state of the immutable ledger represents the latest values for all keys that are included in the chain transaction log. Because the current state represents the latest key values known to a channel, it is sometimes referred to as a world state. Chaincode invocations execute transactions against the current state data of the ledger. To make these chaincode interactions efficient, the latest values of the keys may be stored in a state database. The state database may be simply an indexed view into the chain's transaction log, it can therefore be regenerated from the chain at any time. The state database may automatically be recovered (or generated if needed) upon peer node startup, and before transactions are accepted.

Some benefits of the instant solutions described and depicted herein include a method and system for decentralized prescription refills over a blockchain network. The exemplary embodiments solve the issues of time and trust by extending features of a database such as immutability, digital signatures and being a single source of truth. The exemplary embodiments provide a solution for decentralized prescription refills in a blockchain-based network. The blockchain networks may be homogenous based on the asset type and rules that govern the assets based on the smart contracts.

Blockchain is different from a traditional database in that blockchain is not a central storage, but rather a decentralized, immutable, and secure storage, where nodes must share in changes to records in the storage. Some properties that are inherent in blockchain and which help implement the blockchain include, but are not limited to, an immutable ledger, smart contracts, security, privacy, decentralization, consensus, endorsement, accessibility, and the like, which are further described herein. According to various aspects, the system for decentralized prescription refills over a blockchain network is implemented due to immutable accountability, security, privacy, permitted decentralization, availability of smart contracts, endorsements and accessibility that are inherent and unique to blockchain. In particular, the blockchain ledger data is immutable and that provides for efficient method for decentralized prescription refills over a blockchain network. Also, use of the encryption in the blockchain provides security and builds trust. The smart contract manages the state of the asset to complete the life-cycle. The example blockchains are permission decentralized. Thus, each end user may have its own ledger copy to access. Multiple organizations (and peers) may be on-boarded on the blockchain network. The key organizations may serve as endorsing peers to validate the smart contract execution results, read-set and write-set. In other words, the blockchain inherent features provide for efficient implementation of a method for decentralized prescription refills.

One of the benefits of the example embodiments is that it improves the functionality of a computing system by implementing a method for decentralized prescription refills in blockchain-based systems. Through the blockchain system described herein, a computing system can perform functionality for decentralized prescription refills over blockchain networks by providing access to capabilities such as distributed ledger, peers, encryption technologies, MSP, event handling, etc. Also, the blockchain enables to create a business network and make any users or organizations to on-board for participation. As such, the blockchain is not just a database. The blockchain comes with capabilities to create a Business Network of users and on-board/off-board organizations to collaborate and execute service processes in the form of smart contracts.

The example embodiments provide numerous benefits over a traditional database. For example, through the blockchain the embodiments provide for immutable accountability, security, privacy, permitted decentralization, availability of smart contracts, endorsements and accessibility that are inherent and unique to the blockchain.

Meanwhile, a traditional database could not be used to implement the example embodiments because it does not bring all parties on the business network, it does not create trusted collaboration and does not provide for an efficient storage of digital assets. The traditional database does not provide for a tamper proof storage and does not provide for preservation of the digital assets being stored. Thus, the proposed method for decentralized prescription refills over blockchain networks cannot be implemented in the traditional database.

Meanwhile, if a traditional database were to be used to implement the example embodiments, the example embodiments would have suffered from unnecessary drawbacks such as search capability, lack of security and slow speed of transactions. Additionally, the automated method for decentralized prescription refills over the blockchain network would simply not be possible.

Accordingly, the example embodiments provide for a specific solution to a problem in the arts/field of prescription refills over the blockchain networks.

The example embodiments also change how data may be stored within a block structure of the blockchain. For example, a digital asset data may be securely stored within a certain portion of the data block (i.e., within header, data segment, or metadata). By storing the digital asset data within data blocks of a blockchain, the digital asset data may be appended to an immutable blockchain ledger through a hash-linked chain of blocks. In some embodiments, the data block may be different than a traditional data block by having a personal data associated with the digital asset not stored together with the assets within a traditional block structure of a blockchain. By removing the personal data associated with the digital asset, the blockchain can provide the benefit of anonymity based on immutable accountability and security.

According to the exemplary embodiments, a method and system for enabling travelers to refill their prescriptions when they travel abroad or to an unfamiliar location are provided. The exemplary embodiments may use a blockchain to process and store the information related to medical insurance, medical conditions, patient's allergies, etc. The blockchain may also provide for required identification mechanisms to verify the identity of a patient who needs a prescription refill. Through blockchain enforced contracts, the system may ensure that only medications that are deemed safe and urgent can be obtained by the requesting patient. Additionally, the exemplary embodiments may use special contracts to ensure that medications that may be damaging for patients due to allergic reactions are not provided to them accidentally. One exemplary embodiment may ensure that local (i.e., foreign) legislations are followed when the prescriptions are filled for a traveling patient(s).

The exemplary embodiments may, advantageously, provide for immediacy of medication availability and may minimize the health risks. In one embodiment, the system can leverage other blockchains that contain relevant information such as global records of medication(s) being dispensed. The smart contracts may be used to calculate an appropriate quantity of the medication to be provided given duration of a trip. The exemplary embodiments may make it easier to implement/update Drug Supply Chain Security Act (DSCSA) regulations and may provide for an optimized distribution of the medications. One exemplary embodiment may incorporate elements of Internet of Things (IoT) for tracking the medications.

The method and system of the exemplary embodiments may not only link the patience's prescription/medical history, but may also tie in the drug supply chain assurance (provenance/and proof point of drug quality) through the blockchain. Thus, the system may provide for linking of the prescription authorization on immutable ledger managed by user consent with drug supply chain assurance by provenance of the local drug supply in line with the local laws for adherence to controlled substance use, etc. The system may provide a fill/no-fill determination based on execution of the smart contract on a pharmacy node. Specific actions/approvals can be done including reputable "disaster relief organizations." A "pharmacy without borders" based on the exemplary system could provide an emergency-triggered approval of certain drugs to a specific location affected by a natural disaster or an epidemic, etc. It would be possible to raise funds for a particular medication and its delivery and to track distribution to specific pharmacies or "virtually enabled pharmacies." In case of a disaster, mobile pharmacies/distribution centers may be situated at strategically placed locations. The system may enable for targeted funding, i.e. tracking funds spent by the "disaster relief organizations" on a given medication.

According to the exemplary embodiments, there are multiple blockchain entities that may be involved: pharmacies (peer nodes), doctors issuing prescriptions, insurance companies paying for the prescriptions, and patients that need to refill their prescriptions. The patient peer may be implemented on a mobile device (e.g., a Smart Phone). These entities may not trust each other fully and may be highly distributed. Additionally, there is a prescription equivalence table that may be used by the pharmacy node to provide generic medications with the same or equivalent components of the original prescription. An insurance coverage table may be used to determine the medications covered by each insurance policy. To enable a "pharmacy without borders," it is necessary to verify patient's identity and facilitate the exchange of relevant medical information (allergies, or pre-existing conditions) among geographically distributed entities that may not trust each other completely. Additionally, healthcare-related data requires stringent privacy protections, so it is necessary to enforce strong confidentiality in the dissemination of information on need-to-know bases and to ensure appropriate authorization of the patient. Certain medications may be restricted from this service, because of a potential abuse for a non-intended population (e.g., recreational drugs). Each prescription has a validity period, after which it cannot be filled at any pharmacy. Finally, in one embodiment, to verify that the patient is indeed traveling, external information may be retrieved from the blockchain (e.g., a boarding pass, a proof of ticket purchase, a proof of check-in at airport, a credit card bill, etc.). Other options may include a set of credentials, certificates, receipts, and, finally, some kind of "live proof" such as an on-demand code to be texted to a patient's mobile phone (which is difficult to spoof).

According to one embodiment, the blockchain is used as a ledger to publish information about prescriptions of different patients. For privacy reasons, the information about medical conditions and prescriptions may be hidden from all pharmacies until a patient requests a prescription refill. To this end, each patient is assigned a cryptographic secret (i.e., a key) that unveils the patient's information when he or she sends a request to a pharmacy to get a prescription refill. A method, according to the exemplary embodiments, may include the following:

A doctor issues a prescription for a patient. The prescription is cryptographically protected using keys owned by the patient. The prescription is published in the blockchain. The blockchain record may include:
a. Patients allergies retrieved from the medical records. For each allergy, a rule in the contract is specified to show that a certain component/medicine cannot be filled for the patient;
b. How many refills and how often they can be refilled;
c. A deadline that shows until when a subscription is valid;
d. An identification method to verify that the patient is requesting a refill.

A patient may add delegation for picking up the medicine in the blockchain with a validity delegation deadline within a geographical area;

A prescription-verification smart contract may be defined to verify that a person X may get prescription Y now at a location Z.

The prescription verification smart contract may include:
a. An identification method to verify the patient who is requesting a refill or verify the authorized third party (k out of N factors that prove patient is there). In one embodiment, this may not be a part of the contract and it is verified by the pharmacist, in an off-chain authentication process;
b. Patients' allergies retrieved from the medical records. For each allergy, a rule in the contract is specified to show that a certain component/medicine cannot be filled for the patient;
c. How many refills are available for this prescription;
d. How often the prescription can be refilled;

e. A deadline indicating until when a subscription is valid;
f. Contract that calls a legislation smart contract from the location;
g. Flexible rules:
  i. If a patient forgot/lost medication can use different information;
  ii. Could not be refilled on time.
    A local-legislation-verification smart contract, where each participant country/place/state may add contracts that regulate the locality. Each country/state/location may have in place a list of medications that cannot be obtained through the pharmacies without borders system. For example, medical marihuana or Valium™ may not be obtained, even if the patient has a valid foreign prescription. These restrictions may be placed on the blockchain as well.
    A smart contract that negotiates the chemical equivalence and the insurance coverage considering the allergies of patients;
    When a patient travels and needs a refill of his medication:
a. He/she may go to a "pharmacy without boarders";
b. The patient or an authorized person provides the identification required by the contract;
c. The patient may provide the key required to read the protected content of the prescription and medical records.
  The prescription is retrieved:
a. Verification of the prescription-based smart contract is made;
b. As part of this verification, a local legislation-based smart contract is performed;
c. Pharmacist verifies availability of the requested medication;
d. If the medication is not available (or too expensive), may verify in the prescription equivalent table if a generic medication may be used.
    A transaction is only recorded onto the blockchain if all conditions are fulfilled.
  The following actions may take place:
a. Store that filled the prescription gets recorded into the blockchain; and
b. A number of times the prescription has been refilled are updated.
    The insurance company node may be notified by another transaction to deduct the entire cost and calculate the out of pocket cost for the patient node.

FIG. 1 illustrates a logic network diagram for decentralized prescription refills over a blockchain network, according to example embodiments.

Referring to FIG. 1, the example network 100 includes a pharmacy node 102 may be connected to other blockchain nodes (patient node 105, doctor node(s) 107, and insurance company node(s) 109. The pharmacy node 102 may be connected to a blockchain 106 that has a ledger 108 for storing patients' data and prescription refill transactions 110. While this example describes in detail only one pharmacy node 102, multiple such nodes may be connected to the blockchain 106. It should be understood that the pharmacy node 102 may include additional components and that some of the components described herein may be removed and/or modified without departing from a scope of the pharmacy node 102 disclosed herein. The pharmacy node 102 may be a computing device or a server computer, or the like, and may include a processor 104, which may be a semiconductor-based microprocessor, a central processing unit (CPU), an application specific integrated circuit (ASIC), a field-programmable gate array (FPGA), and/or another hardware device. Although a single processor 104 is depicted, it should be understood that the pharmacy node 102 may include multiple processors, multiple cores, or the like, without departing from the scope of the pharmacy node 102 system.

The pharmacy node 102 may also include a non-transitory computer readable medium 112 that may have stored thereon machine-readable instructions executable by the processor 104. Examples of the machine-readable instructions are shown as 114-120 and are further discussed below. Examples of the non-transitory computer readable medium 112 may include an electronic, magnetic, optical, or other physical storage device that contains or stores executable instructions. For example, the non-transitory computer readable medium 112 may be a Random Access memory (RAM), an Electrically Erasable Programmable Read-Only Memory (EEPROM), a hard disk, an optical disc, or other type of storage device.

The processor 104 may fetch, decode, and execute the machine-readable instructions 114 to connect to a blockchain network configured to store patients' data on a blockchain ledger. As discussed above, the blockchain ledger 108 may store prescription refill transactions 110. The blockchain 106 network may be configured to use one or more smart contracts that manage transactions for multiple participating nodes.

The processor 104 may fetch, decode, and execute the machine-readable instructions 116 to receive a request from a patient node 105 for a prescription refill, the request contains a secret key of a patient. The processor 104 may fetch, decode, and execute the machine-readable instructions 118 to extract the secret key from the request to verify a patient's identity. The processor 104 may fetch, decode, and execute the machine-readable instructions 120 to execute a smart contract to: (a) decrypt a prescription data located on the ledger by an application of the secret key; (b) retrieve patient's allergy records from the ledger 108 to check the allergy records against the prescription data; (c) determine a number of remaining refills from the prescription data; (d) check validity of the prescription data based on an expiration date; and commit a prescription refill transaction to the blockchain 106 based on a successful execution of (b)-(d).

Figure 2A:
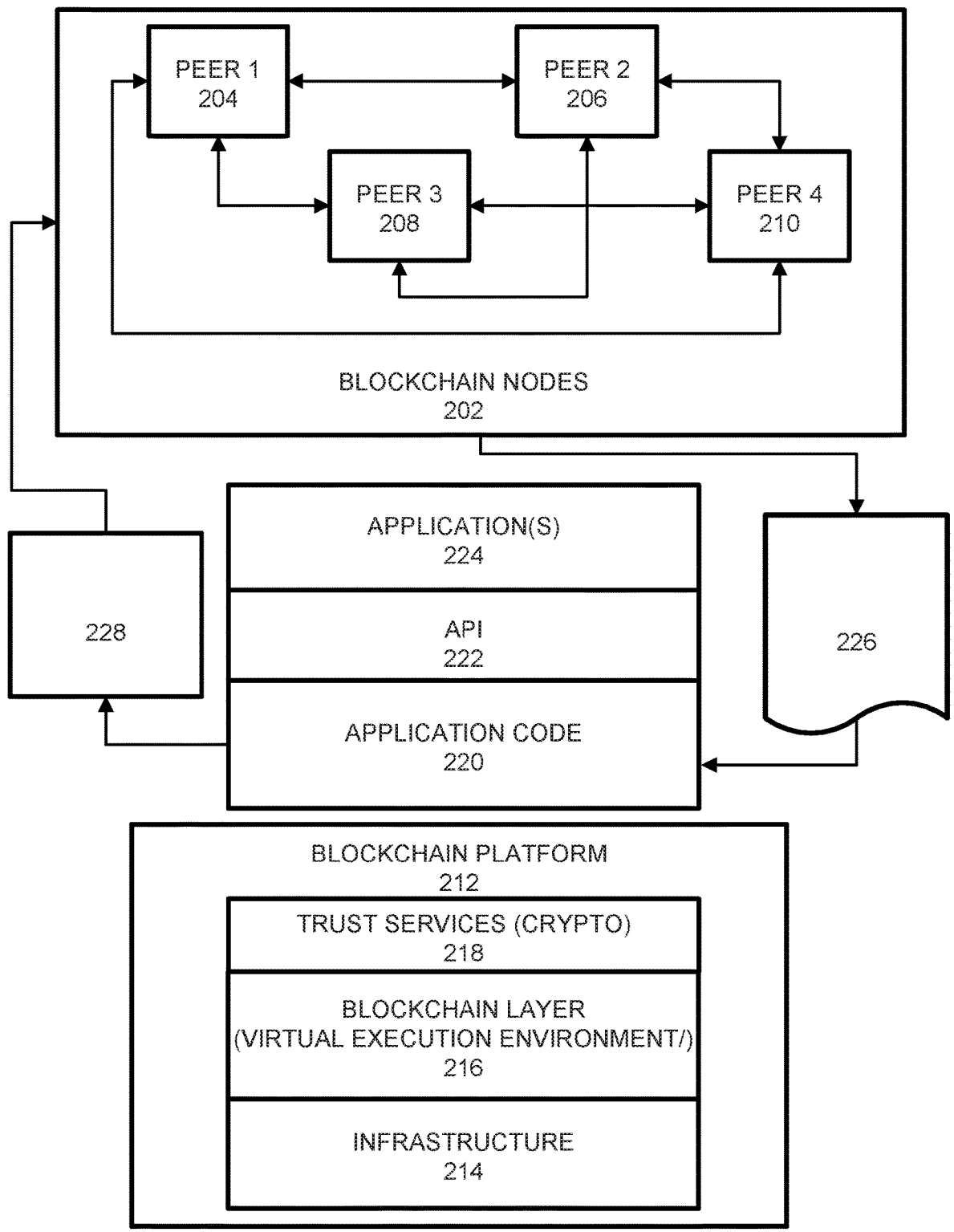
FIG. 2A illustrates an example peer node configuration, according to example embodiments.

FIG. 2A illustrates a blockchain architecture configuration 200, according to example embodiments. Referring to FIG. 2A, the blockchain architecture 200 may include certain blockchain elements, for example, a group of blockchain nodes 202. The blockchain nodes 202 may include one or more nodes 204-210 (these four nodes are depicted by example only). These nodes participate in a number of activities, such as blockchain transaction addition and validation process (consensus). One or more of the blockchain nodes 204-210 may endorse transactions based on endorsement policy and may provide an ordering service for all blockchain nodes in the architecture 200. A blockchain node may initiate a blockchain authentication and seek to write to a blockchain immutable ledger stored in blockchain layer 216, a copy of which may also be stored on the underpinning physical infrastructure 214. The blockchain configuration may include one or more applications 224 which are linked to application programming interfaces (APIs) 222 to access and execute stored program/application code 220 (e.g., chaincode, smart contracts, etc.) which can be created according to a customized configuration sought by participants and can maintain their own state, control their own assets, and receive external information. This can be deployed as a transaction and installed, via appending to the distributed ledger, on all blockchain nodes 204-210.

The blockchain base or platform 212 may include various layers of blockchain data, services (e.g., cryptographic trust services, virtual execution environment, etc.), and underpinning physical computer infrastructure that may be used to receive and store new transactions and provide access to auditors which are seeking to access data entries. The blockchain layer 216 may expose an interface that provides access to the virtual execution environment necessary to process the program code and engage the physical infrastructure 214. Cryptographic trust services 218 may be used to verify transactions such as asset exchange transactions and keep information private.

The blockchain architecture configuration of FIG. 2A may process and execute program/application code 220 via one or more interfaces exposed, and services provided, by blockchain platform 212. The code 220 may control blockchain assets. For example, the code 220 can store and transfer data, and may be executed by nodes 204-210 in the form of a smart contract and associated chaincode with conditions or other code elements subject to its execution. As a non-limiting example, smart contracts may be created to execute reminders, updates, and/or other notifications subject to the changes, updates, etc. The smart contracts can themselves be used to identify rules associated with authorization and access requirements and usage of the ledger. For example, the prescription request information 226 may be processed by one or more processing entities (e.g., virtual machines) included in the blockchain layer 216. The result 228 may include data blocks reflecting a number of the remaining refills available under the prescription. The physical infrastructure 214 may be utilized to retrieve any of the data or information described herein.

Within chaincode, a smart contract may be created via a high-level application and programming language, and then written to a block in the blockchain. The smart contract may include executable code which is registered, stored, and/or replicated with a blockchain (e.g., distributed network of blockchain peers). A transaction is an execution of the smart contract code which can be performed in response to conditions associated with the smart contract being satisfied. The executing of the smart contract may trigger a trusted modification(s) to a state of a digital blockchain ledger. The modification(s) to the blockchain ledger caused by the smart contract execution may be automatically replicated throughout the distributed network of blockchain peers through one or more consensus protocols.

The smart contract may write data to the blockchain in the format of key-value pairs. Furthermore, the smart contract code can read the values stored in a blockchain and use them in application operations. The smart contract code can write the output of various logic operations into the blockchain. The code may be used to create a temporary data structure in a virtual machine or other computing platform. Data written to the blockchain can be public and/or can be encrypted and maintained as private. The temporary data that is used/generated by the smart contract is held in memory by the supplied execution environment and then deleted once the data needed for the blockchain is identified.

A chaincode may include the code interpretation of a smart contract, with additional features. As described herein, the chaincode may be program code deployed on a computing network, where it is executed and validated by chain validators together during a consensus process. The chaincode receives a hash and retrieves from the blockchain a hash associated with the data template created by use of a previously stored feature extractor. If the hashes of the hash identifier and the hash created from the stored identifier template data match, then the chaincode sends an authorization key to the requested service. The chaincode may write to the blockchain data associated with the cryptographic details. In FIG. 2A, a prescription refill transaction may include execution of the smart contract. One function may be to commit a transaction related to execution of the smart contract on the ledger for recording of the prescription refill data, which may be provided to one or more of the nodes 204-210.

Figure 2B:
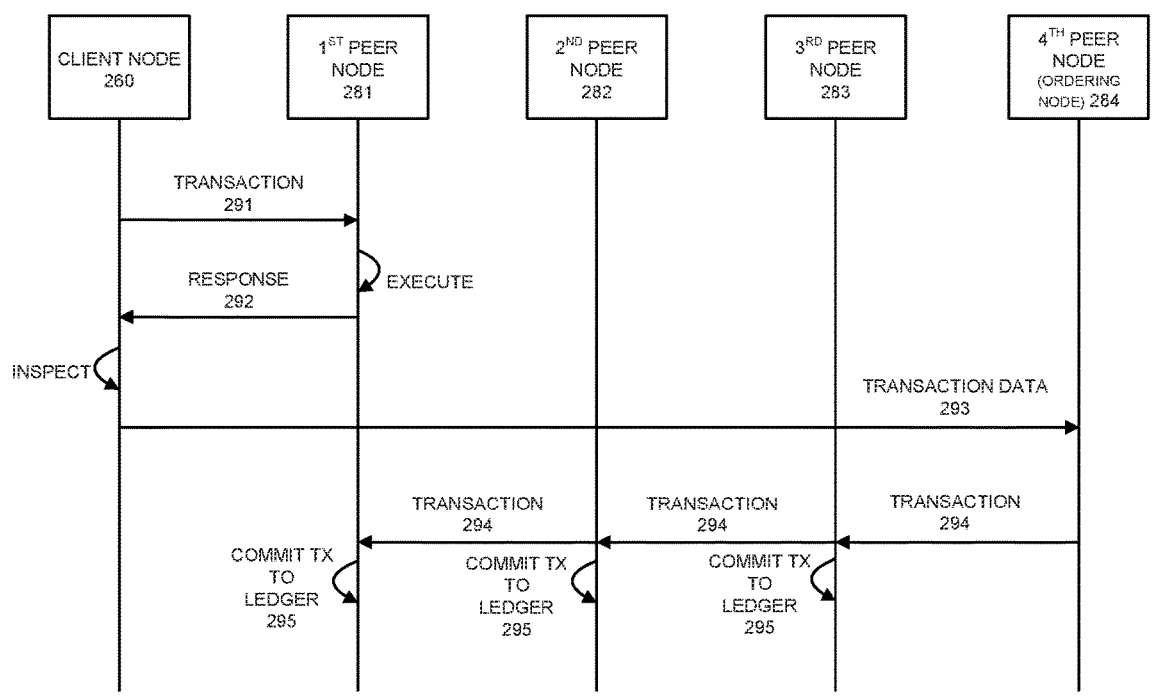
FIG. 2B illustrates a further peer node configuration, according to example embodiments.

FIG. 2B illustrates an example of a transactional flow 250 between nodes of the blockchain in accordance with an example embodiment. Referring to FIG. 2B, the transaction flow may include a transaction proposal 291 sent by an application client node 260 to an endorsing peer node 281. The endorsing peer 281 may verify the client signature and execute a chaincode function to initiate the transaction. The output may include the chaincode results, a set of key/value versions that were read in the chaincode (read set), and the set of keys/values that were written in chaincode (write set). The proposal response 292 is sent back to the client 260 along with an endorsement signature, if approved. The client 260 assembles the endorsements into a transaction payload 293 and broadcasts it to an ordering service node 284. The ordering service node 284 then delivers ordered transactions as blocks to all peers 281-283 on a channel. Before committal to the blockchain, each peer 281-283 may validate the transaction. For example, the peers may check the endorsement policy to ensure that the correct allotment of the specified peers have signed the results and authenticated the signatures against the transaction payload 293.

Referring again to FIG. 2B, the client node 260 initiates the transaction 291 by constructing and sending a request to the peer node 281, which is an endorser. The client 260 may include an application leveraging a supported software development kit (SDK), such as NODE, JAVA, PYTHON, and the like, which utilizes an available API to generate a transaction proposal. The proposal is a request to invoke a chaincode function so that data can be read and/or written to the ledger (i.e., write new key value pairs for the assets). The SDK may serve as a shim to package the transaction proposal into a properly architected format (e.g., protocol buffer over a remote procedure call (RPC)) and take the client's cryptographic credentials to produce a unique signature for the transaction proposal.

In response, the endorsing peer node 281 may verify (a) that the transaction proposal is well formed, (b) the transaction has not been submitted already in the past (replay-attack protection), (c) the signature is valid, and (d) that the submitter (client 260, in the example) is properly authorized to perform the proposed operation on that channel. The endorsing peer node 281 may take the transaction proposal inputs as arguments to the invoked chaincode function. The chaincode is then executed against a current state database to produce transaction results including a response value, read set, and write set. However, no updates are made to the ledger at this point. In 292, the set of values along with the endorsing peer node's 281 signature is passed back as a proposal response 292 to the SDK of the client 260 which parses the payload for the application to consume.

In response, the application of the client 260 inspects/verifies the endorsing peers' signatures and compares the proposal responses to determine if the proposal response is the same. If the chaincode only queried the ledger, the application would inspect the query response and would typically not submit the transaction to the ordering node service 284. If the client application intends to submit the transaction to the ordering node service 284 to update the ledger, the application determines if the specified endorsement policy has been fulfilled before submitting (i.e., did all peer nodes necessary for the transaction endorse the transaction). Here, the client may include only one of multiple parties to the transaction. In this case, each client may have their own endorsing node, and each endorsing node will need to endorse the transaction. The architecture is such that even if an application selects not to inspect responses or otherwise forwards an unendorsed transaction, the endorsement policy will still be enforced by peers and upheld at the commit validation phase.

After successful inspection, in step 293 the client 260 assembles endorsements into a transaction and broadcasts the transaction proposal and response within a transaction message to the ordering node 284. The transaction may contain the read/write sets, the endorsing peers' signatures and a channel ID. The ordering node 284 does not need to inspect the entire content of a transaction in order to perform its operation. Instead, the ordering node 284 may simply receive transactions from all channels in the network, order them chronologically by channel, and create blocks of transactions per channel.

The blocks of the transaction are delivered from the ordering node 284 to all peer nodes 281-283 on the channel. The transactions 294 within the block are validated to ensure any endorsement policy is fulfilled and to ensure that there have been no changes to ledger state for read set variables since the read set was generated by the transaction execution. Transactions in the block are tagged as being valid or invalid. Furthermore, in step 295 each peer node 281-283 appends the block to the channel's chain, and for each valid transaction the write sets are committed to current state database. An event is emitted, to notify the client application that the transaction (invocation) has been immutably appended to the chain, as well as to notify whether the transaction was validated or invalidated.

Figure 3:
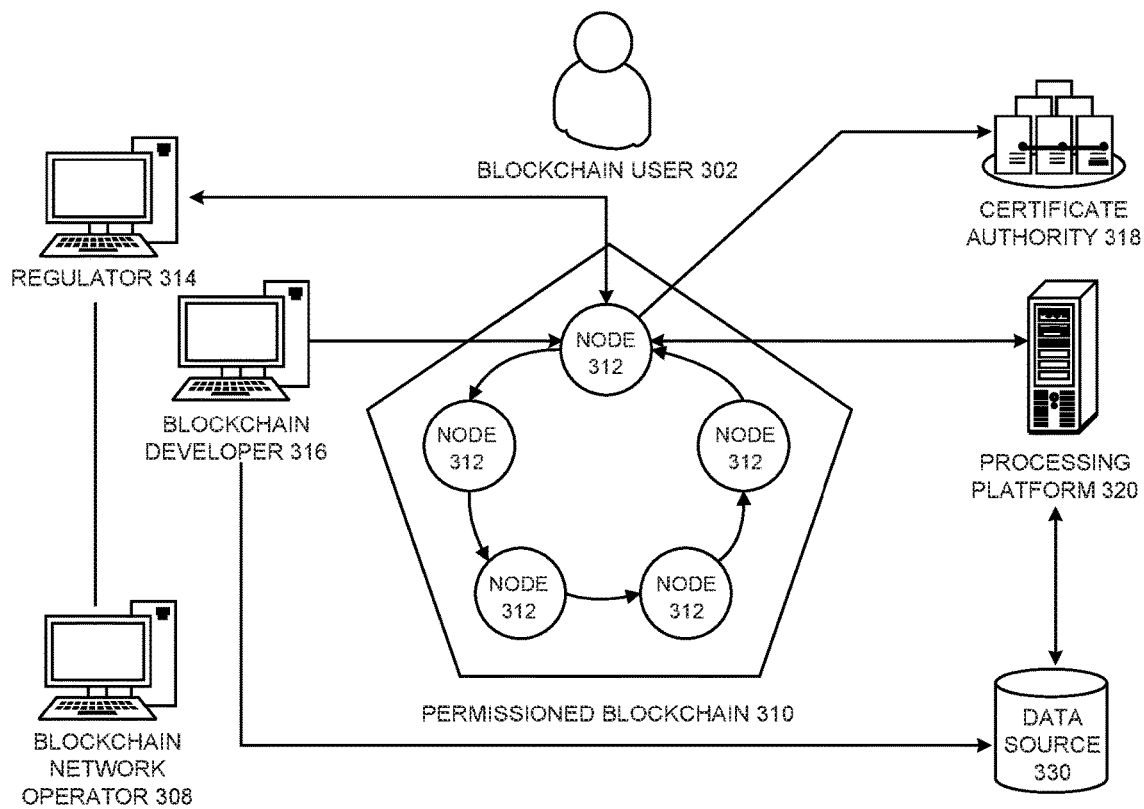
FIG. 3 illustrates a permissioned network, according to example embodiments.

FIG. 3 illustrates an example of a permissioned blockchain network 300, which features a distributed, decentralized peer-to-peer architecture, and a certificate authority 318 managing user roles and permissions. In this example, the blockchain user 302 may submit a transaction to the permissioned blockchain network 310. In this example, the transaction can be a deploy, invoke or query, and may be issued through a client-side application leveraging an SDK, directly through a REST API, or the like. Trusted business networks may provide access to regulator systems 314, such as auditors (the Securities and Exchange Commission in a U.S. equities market, for example). Meanwhile, a blockchain network operator system of nodes 308 manages member permissions, such as enrolling the regulator system 310 as an "auditor" and the blockchain user 302 as a "client." An auditor could be restricted only to querying the ledger whereas a client could be authorized to deploy, invoke, and query certain types of chaincode.

A blockchain developer system 316 writes chaincode and client-side applications. The blockchain developer system 316 can deploy chaincode directly to the network through a REST interface. To include credentials from a traditional data source 330 in chaincode, the developer system 316 could use an out-of-band connection to access the data. In this example, the blockchain user 302 connects to the network through a peer node 312. Before proceeding with any transactions, the peer node 312 retrieves the user's enrollment and transaction certificates from the certificate authority 318. In some cases, blockchain users must possess these digital certificates in order to transact on the permissioned blockchain network 310. Meanwhile, a user attempting to drive chaincode may be required to verify their credentials on the traditional data source 330. To confirm the user's authorization, chaincode can use an out-of-band connection to this data through a traditional processing platform 320.

Figure 4A:
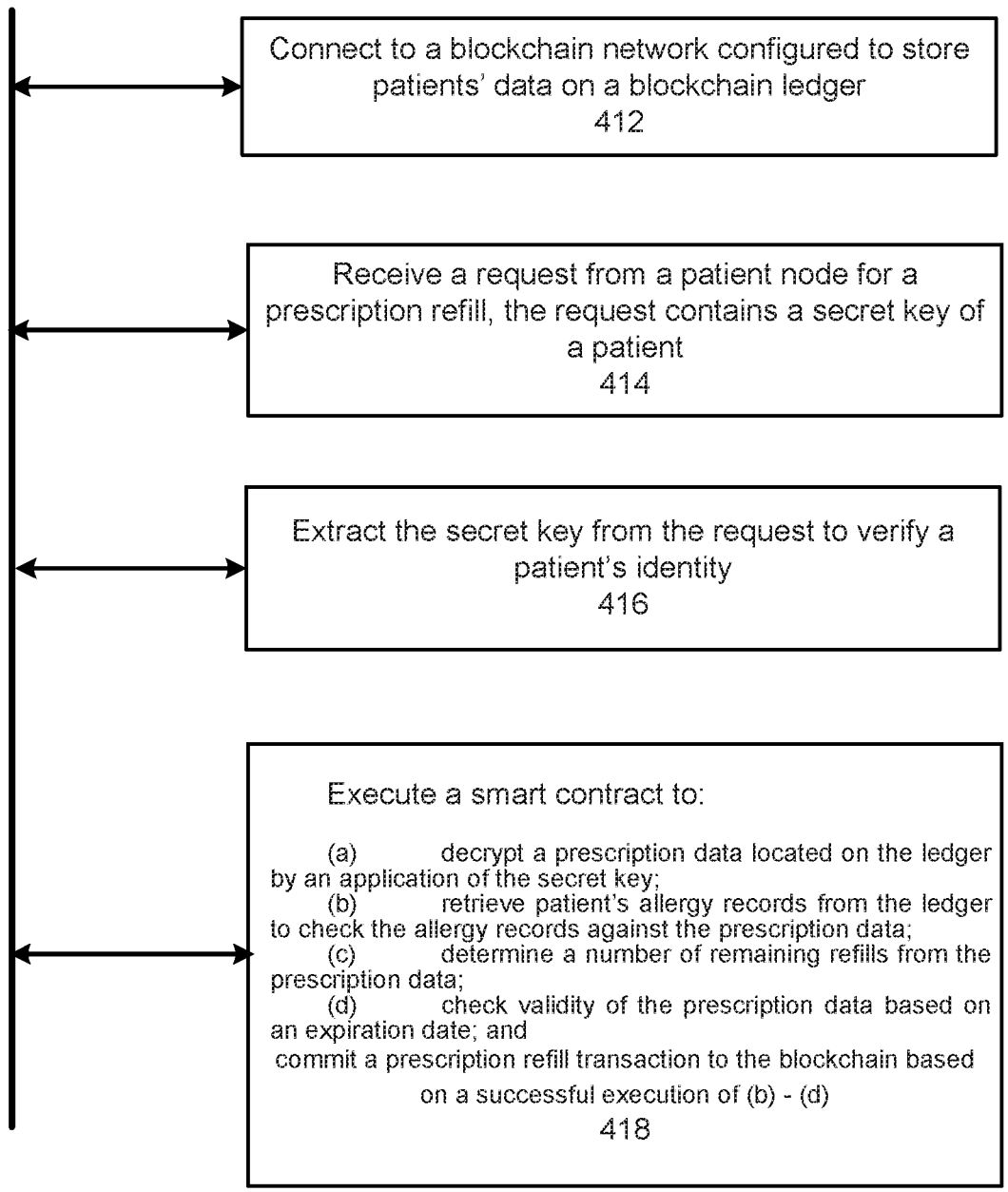
FIG. 4A illustrates a flow diagram, according to example embodiments.

FIG. 4A illustrates a flow diagram 400 of an example method of decentralized prescription refills over blockchain networks, according to example embodiments. Referring to FIG. 4A, the method 400 may include one or more of the steps described below.

FIG. 4A illustrates a flow chart of an example method executed by the pharmacy node 102 (see FIG. 1). It should be understood that method 400 depicted in FIG. 4A may include additional operations and that some of the operations described therein may be removed and/or modified without departing from the scope of the method 400. The description of the method 400 is also made with reference to the features depicted in FIG. 1 for purposes of illustration. Particularly, the processor 104 of the pharmacy node 102 may execute some or all of the operations included in the method 400.

With reference to FIG. 4A, at block 412, the processor 104 may connect to a blockchain network configured to store patients' data on a blockchain ledger. At block 414, the processor 104 may receive a request from a patient node for a prescription refill. The request may contain a secret key of a patient. At block 416, the processor 104 may extract the secret key from the request to verify a patient's identity. At block 418, the processor 104 may execute a smart contract to: (a) decrypt a prescription data located on the ledger by an application of the secret key; (b) retrieve patient's allergy records from the ledger to check the allergy records against the prescription data; (c) determine a number of remaining refills from the prescription data; (d) check validity of the prescription data based on an expiration date; and commit a prescription refill transaction to the blockchain 106 based on a successful execution of (b)-(d).

Figure 4B:
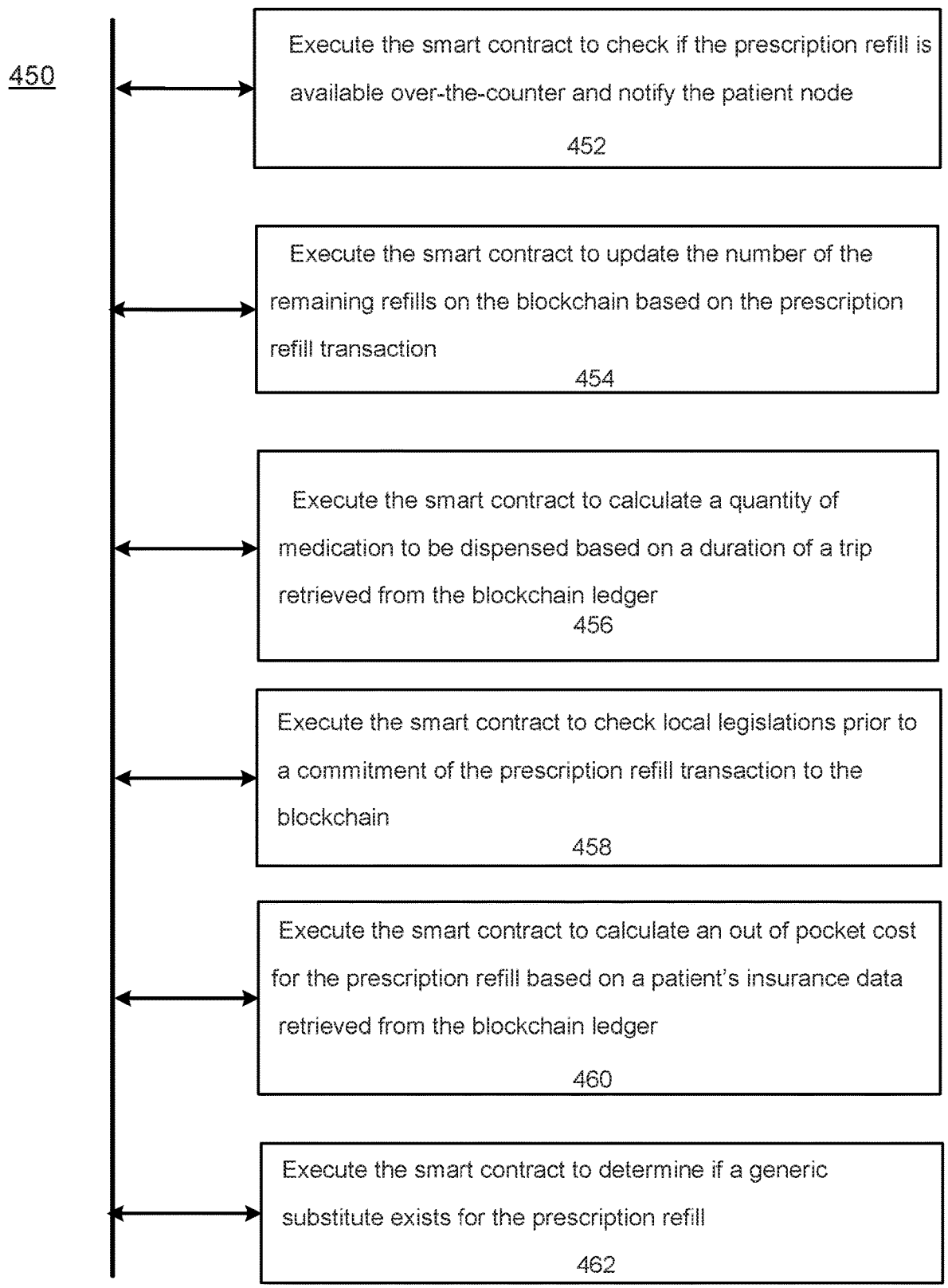
FIG. 4B illustrates a further flow diagram, according to example embodiments.

FIG. 4B illustrates a flow diagram 450 of an example method of decentralized prescription refill in a blockchain network, according to example embodiments. Referring to FIG. 4B, the method 450 may also include one or more of the following steps. At block 452, the processor 104 may execute the smart contract to check if the prescription refill is available over-the-counter and notify the patient node. At block 454, the processor 104 may execute the smart contract to update the number of the remaining refills on the blockchain based on the prescription refill transaction. At block 456, the processor 104 may execute the smart contract to calculate a quantity of medication to be dispensed based on a duration of a trip retrieved from the blockchain ledger. At block 458, the processor 104 may execute the smart contract to check local legislations prior to a commitment of the prescription refill transaction to the blockchain. At block 460, the processor 104 may execute the smart contract to calculate an out of pocket cost for the prescription refill based on a patient's insurance data retrieved from the blockchain ledger. At block 462, the processor 104 may execute the smart contract to determine if a generic substitute exists for the prescription refill.

Note that while the prescription may be a refill and the origin country jurisdiction may have allowed a combination, the host country may reflect adherence to local jurisdiction and suggest n alternative generic medication. This decision and prescription fulfillment may be recorded in patient health record on the blockchain and may be later used for analysis by health care service provider and may trigger a corrective action upon patient's return to his original country.

Figure 5A:
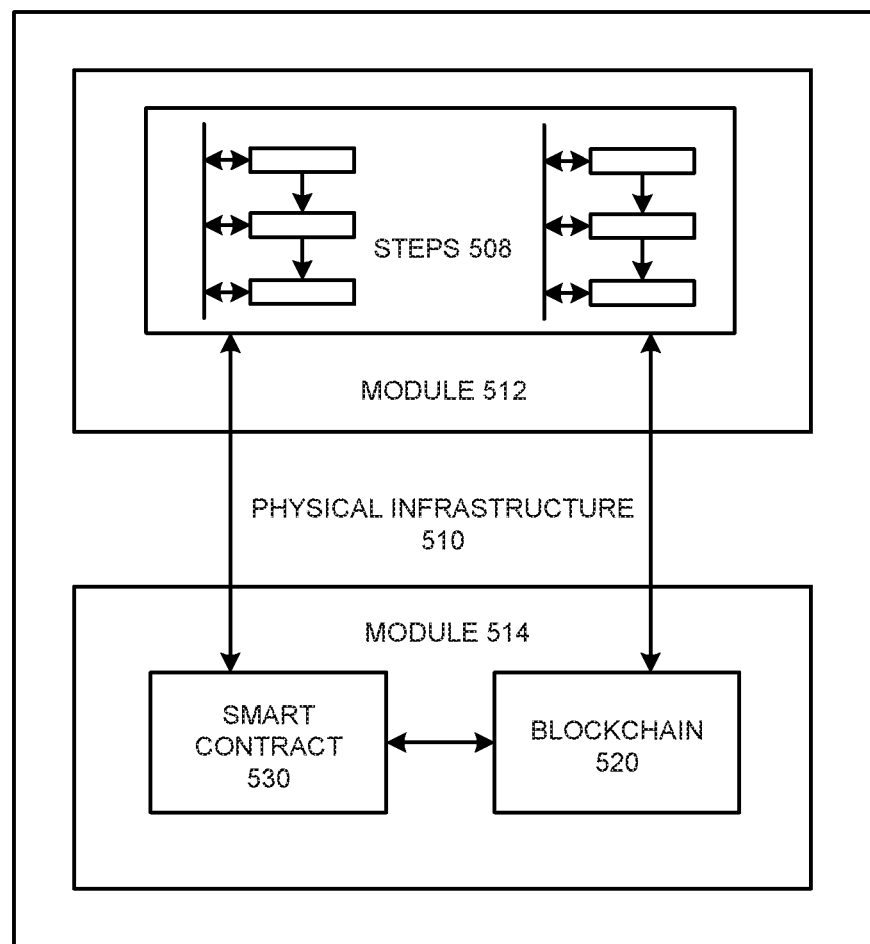
FIG. 5A illustrates an example system configured to perform one or more operations described herein, according to example embodiments.

FIG. 5A illustrates an example system 500 that includes a physical infrastructure 510 configured to perform various operations according to example embodiments. Referring to FIG. 5A, the physical infrastructure 510 includes a module 512 and a module 514. The module 514 includes a blockchain 520 and a smart contract 530 (which may reside on the blockchain 520), that may execute any of the operational steps 508 (in module 512) included in any of the example embodiments. The steps/operations 508 may include one or more of the embodiments described or depicted and may represent output or written information that is written or read from one or more smart contracts 530 and/or blockchains 520. The physical infrastructure 510, the module 512, and the module 514 may include one or more computers, servers, processors, memories, and/or wireless communication devices. Further, the module 512 and the module 514 may be a same module.

Figure 5B:
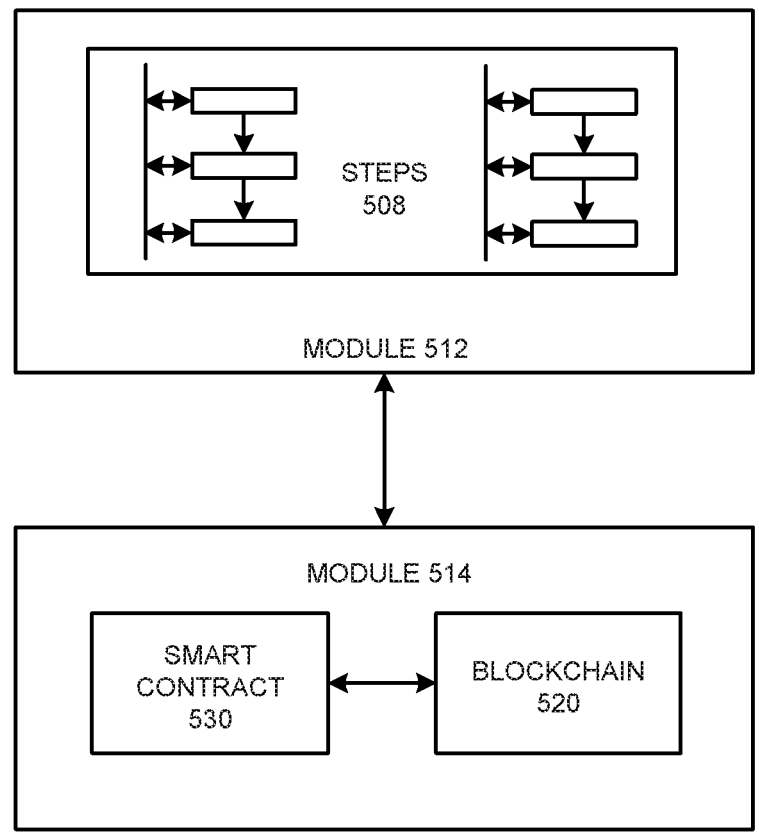
FIG. 5B illustrates a further example system configured to perform one or more operations described herein, according to example embodiments.

FIG. 5B illustrates an example system 540 configured to perform various operations according to example embodiments. Referring to FIG. 5B, the system 540 includes a module 512 and a module 514. The module 514 includes a blockchain 520 and a smart contract 530 (which may reside on the blockchain 520), that may execute any of the operational steps 508 (in module 512) included in any of the example embodiments. The steps/operations 508 may include one or more of the embodiments described or depicted and may represent output or written information that is written or read from one or more smart contracts 530 and/or blockchains 520. The physical infrastructure 510, the module 512, and the module 514 may include one or more computers, servers, processors, memories, and/or wireless communication devices. Further, the module 512 and the module 514 may be a same module.

Figure 5C:
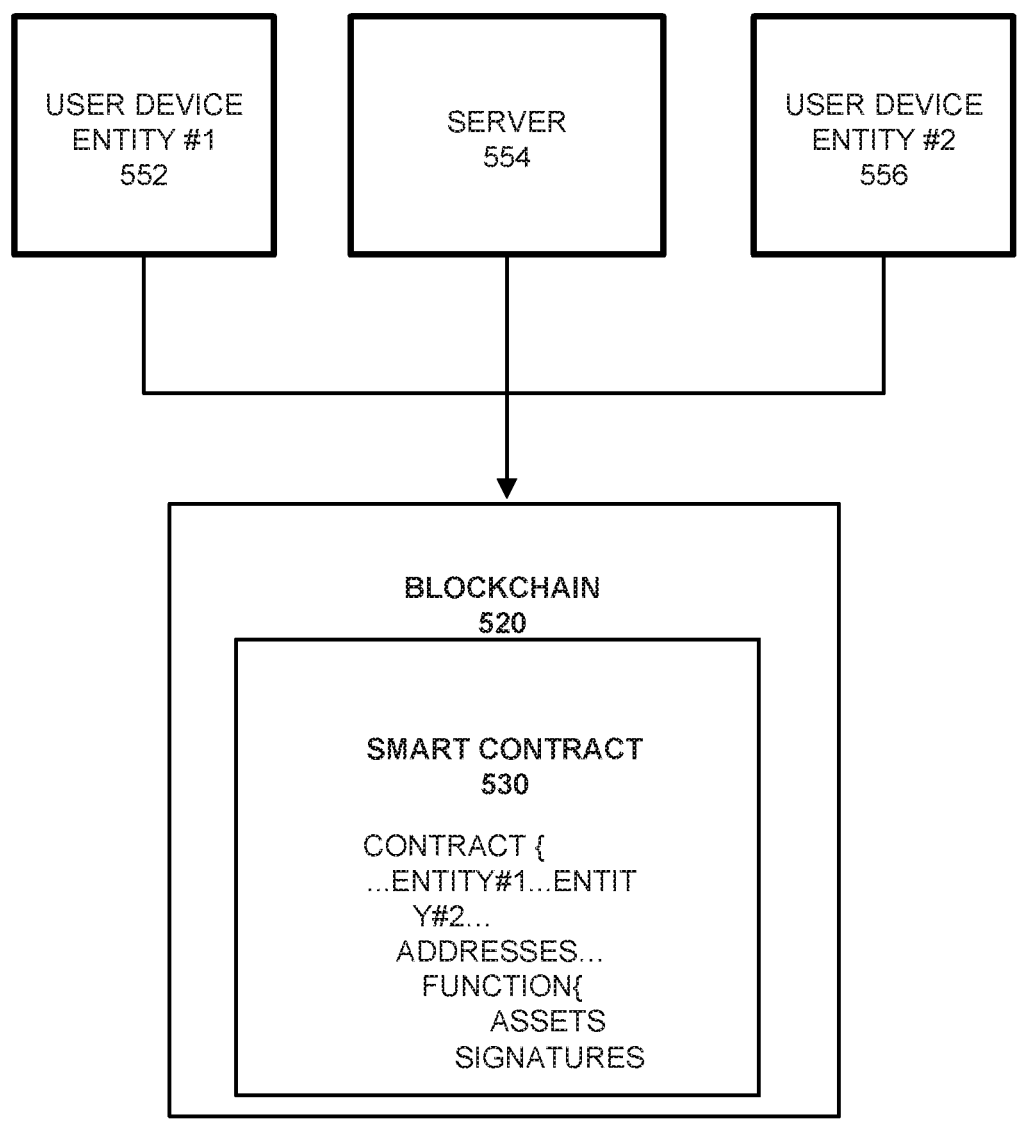
FIG. 5C illustrates a smart contract configuration among contracting parties and a mediating server configured to enforce the smart contract terms on the blockchain according to example embodiments.

FIG. 5C illustrates an example smart contract configuration among contracting parties and a mediating server configured to enforce the smart contract terms on the blockchain according to example embodiments. Referring to FIG. 5C, the configuration 550 may represent a communication session, an asset transfer session or a process or procedure that is driven by a smart contract 530 which explicitly identifies one or more user devices 552 and/or 556. The execution, operations and results of the smart contract execution may be managed by a server 554. Content of the smart contract 530 may require digital signatures by one or more of the entities 552 and 556 which are parties to the smart contract transaction. The results of the smart contract execution may be written to a blockchain 520 as a blockchain transaction. The smart contract 530 resides on the blockchain 520 which may reside on one or more computers, servers, processors, memories, and/or wireless communication devices.

Figure 5D:
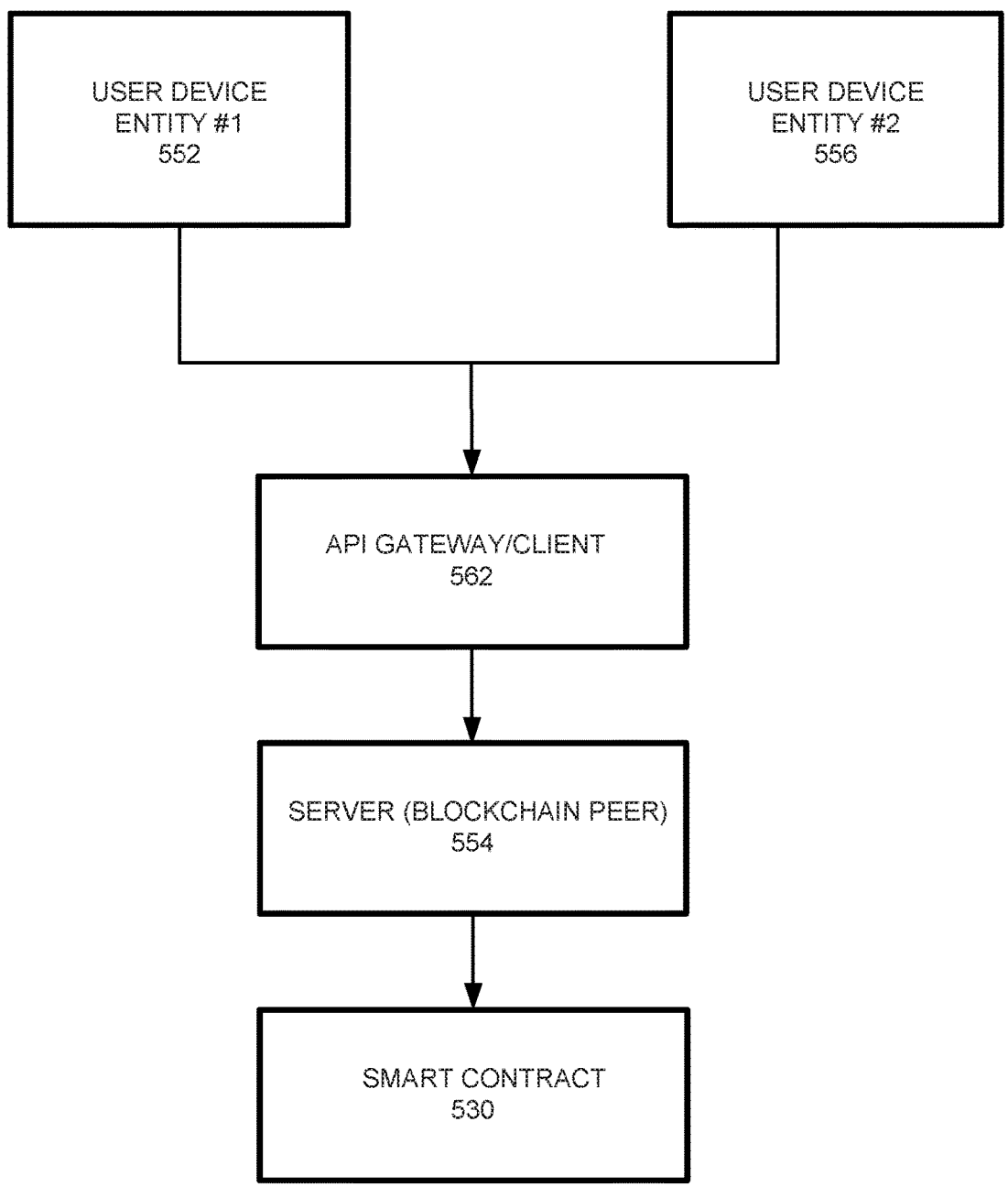
FIG. 5D illustrates another additional example system, according to example embodiments.

FIG. 5D illustrates a common interface for accessing logic and data of a blockchain, according to example embodiments. Referring to the example of FIG. 5D, an application programming interface (API) gateway 562 provides a common interface for accessing blockchain logic (e.g., smart contract 530 or other chaincode) and data (e.g., distributed ledger, etc.) In this example, the API gateway 562 is a common interface for performing transactions (invoke, queries, etc.) on the blockchain by connecting one or more entities 552 and 556 to a blockchain peer (i.e., server 554). Here, the server 554 is a blockchain network peer component that holds a copy of the world state and a distributed ledger allowing clients 552 and 556 to query data on the world state as well as submit transactions into the blockchain network where, depending on the smart contract 530 and endorsement policy, endorsing peers will run the smart contracts 530.

The above embodiments may be implemented in hardware, in a computer program executed by a processor, in firmware, or in a combination of the above. A computer program may be embodied on a computer readable medium, such as a storage medium. For example, a computer program may reside in random access memory ("RAM"), flash memory, read-only memory ("ROM"), erasable programmable read-only memory ("EPROM"), electrically erasable programmable read-only memory ("EEPROM"), registers, hard disk, a removable disk, a compact disk read-only memory ("CD-ROM"), or any other form of storage medium known in the art.

An exemplary storage medium may be coupled to the processor such that the processor may read information from, and write information to, the storage medium. In the alternative, the storage medium may be integral to the processor. The processor and the storage medium may reside in an application specific integrated circuit ("ASIC"). In the alternative, the processor and the storage medium may reside as discrete components. For example, FIG. 6 illustrates an example computer system architecture 600, which may represent or be integrated in any of the above-described components, etc.

Figure 6A:
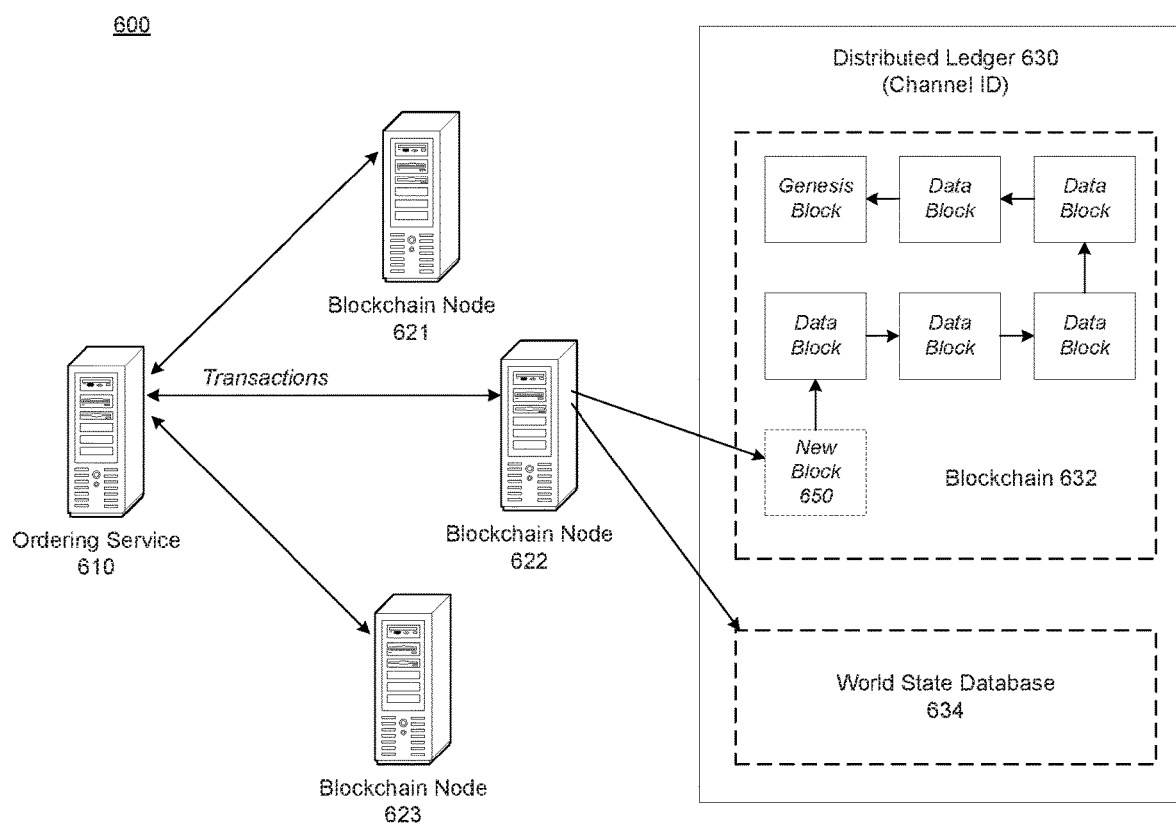
FIG. 6A illustrates a process of new data being added to a database, according to example embodiments.
Figure 6B:
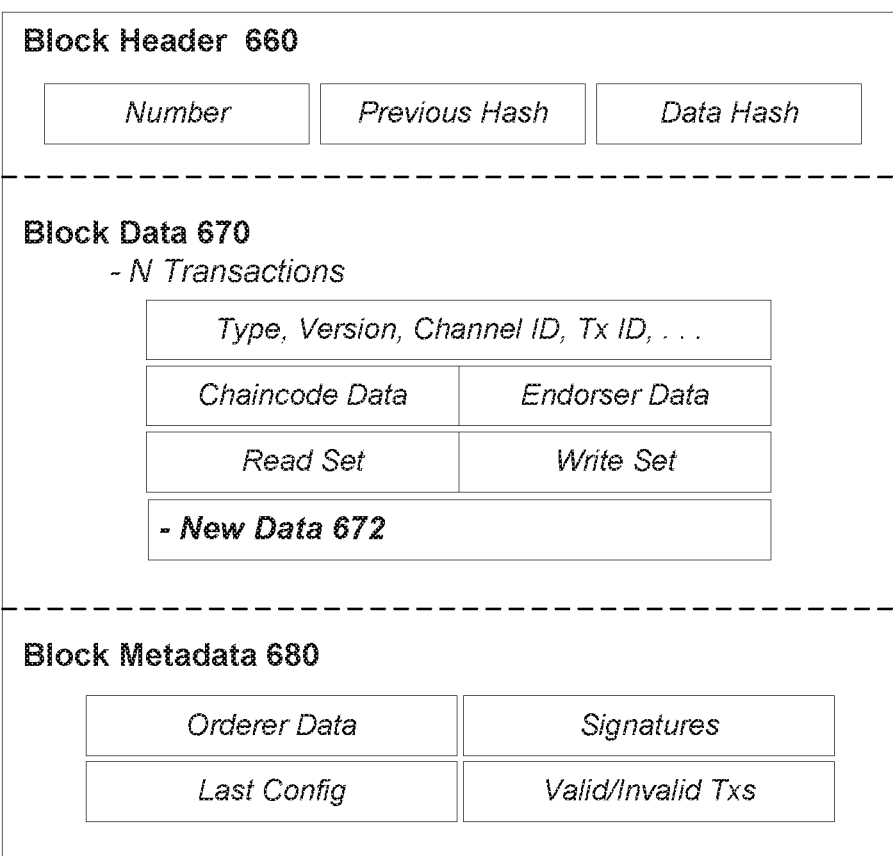
FIG. 6B illustrates contents a data block including the new data, according to example embodiments.

FIG. 6A illustrates a process 600 of a new block being added to a distributed ledger 630, according to example embodiments, and FIG. 6B illustrates contents of a block structure 650 for blockchain, according to example embodiments. Referring to FIG. 6A, clients (not shown) may submit transactions to blockchain nodes 621, 622, and/or 623. Clients may be instructions received from any source to enact activity on the blockchain 630. As an example, clients may be applications that act on behalf of a requester, such as a device, person or entity to propose transactions for the blockchain. The plurality of blockchain peers (e.g., blockchain nodes 621, 622, and 623) may maintain a state of the blockchain network and a copy of the distributed ledger 630. Different types of blockchain nodes/peers may be present in the blockchain network including endorsing peers which simulate and endorse transactions proposed by clients and committing peers which verify endorsements, validate transactions, and commit transactions to the distributed ledger 630. In this example, the blockchain nodes 621, 622, and 623 may perform the role of endorser node, committer node, or both.

The distributed ledger 630 includes a blockchain 632 which stores immutable, sequenced records in blocks, and a state database 634 (current world state) maintaining a current state of the blockchain 632. One distributed ledger 630 may exist per channel and each peer maintains its own copy of the distributed ledger 630 for each channel of which they are a member. The blockchain 632 is a transaction log, structured as hash-linked blocks where each block contains a sequence of N transactions. Blocks may include various components such as shown in FIG. 6B. The linking of the blocks (shown by arrows in FIG. 6A) may be generated by adding a hash of a prior block's header within a block header of a current block. In this way, all transactions on the blockchain 632 are sequenced and cryptographically linked together preventing tampering with blockchain data without breaking the hash links. Furthermore, because of the links, the latest block in the blockchain 632 represents every transaction that has come before it. The blockchain 632 may be stored on a peer file system (local or attached storage), which supports an append-only blockchain workload.

The current state of the blockchain 632 and the distributed ledger 632 may be stored in the state database 634. Here, the current state data represents the latest values for all keys ever included in the chain transaction log of the blockchain 632. Chaincode invocations execute transactions against the current state in the state database 634. To make these chaincode interactions extremely efficient, the latest values of all keys are stored in the state database 634. The state database 634 may include an indexed view into the transaction log of the blockchain 632, it can therefore be regenerated from the chain at any time. The state database 634 may automatically get recovered (or generated if needed) upon peer startup, before transactions are accepted.

Endorsing nodes receive transactions from clients and endorse the transaction based on simulated results. Endorsing nodes hold smart contracts which simulate the transaction proposals. When an endorsing node endorses a transaction, the endorsing node creates a transaction endorsement which is a signed response from the endorsing node to the client application indicating the endorsement of the simulated transaction. The method of endorsing a transaction depends on an endorsement policy which may be specified within chaincode. An example of an endorsement policy is "the majority of endorsing peers must endorse the transaction." Different channels may have different endorsement policies. Endorsed transactions are forwarded by the client application to ordering service 610.

The ordering service 610 accepts endorsed transactions, orders them into a block, and delivers the blocks to the committing peers. For example, the ordering service 610 may initiate a new block when a threshold of transactions has been reached, a timer times out, or another condition. In the example of FIG. 6A, blockchain node 622 is a committing peer that has received a new data block 650 for storage on blockchain 630.

The ordering service 610 may be made up of a cluster of orderers. The ordering service 610 does not process transactions, smart contracts, or maintain the shared ledger. Rather, the ordering service 610 may accept the endorsed transactions and specifies the order in which those transactions are committed to the distributed ledger 630. The architecture of the blockchain network may be designed such that the specific implementation of 'ordering' (e.g., Solo, Kafka, BFT, etc.) becomes a pluggable component.

Transactions are written to the distributed ledger 630 in a consistent order. The order of transactions is established to ensure that the updates to the state database 634 are valid when they are committed to the network. Unlike a cryptocurrency blockchain system (e.g., Bitcoin, etc.) where ordering occurs through the solving of a cryptographic puzzle, or mining, in this example the parties of the distributed ledger 630 may choose the ordering mechanism that best suits that network.

When the ordering service 610 initializes a new block 650, the new block 650 may be broadcast to committing peers (e.g., blockchain nodes 621, 622, and 623). In response, each committing peer validates the transaction within the new block 650 by checking to make sure that the read set and the write set still match the current world state in the state database 634. Specifically, the committing peer can determine whether the read data that existed when the endorsers simulated the transaction is identical to the current world state in the state database 634. When the committing peer validates the transaction, the transaction is written to the blockchain 632 on the distributed ledger 630, and the state database 634 is updated with the write data from the read-write set. If a transaction fails, that is, if the committing peer finds that the read-write set does not match the current world state in the state database 634, the transaction ordered into a block will still be included in that block, but it will be marked as invalid, and the state database 634 will not be updated.

Referring to FIG. 6B, a block 650 (also referred to as a data block) that is stored on the blockchain 632 of the distributed ledger 630 may include multiple data segments such as a block header 660, block data 670, and block metadata 680. It should be appreciated that the various depicted blocks and their contents, such as block 650 and its contents. Shown in FIG. 6B are merely for purposes of example and are not meant to limit the scope of the example embodiments. In some cases, both the block header 660 and the block metadata 680 may be smaller than the block data 670 which stores transaction data, however, this is not a requirement. The block 650 may store transactional information of N transactions (e.g., 100, 500, 1000, 2000, 3000, etc.) within the block data 670. The block 650 may also include a link to a previous block (e.g., on the blockchain 632 in FIG. 6A) within the block header 660. In particular, the block header 660 may include a hash of a previous block's header. The block header 660 may also include a unique block number, a hash of the block data 670 of the current block 650, and the like. The block number of the block 650 may be unique and assigned in an incremental/sequential order starting from zero. The first block in the blockchain may be referred to as a genesis block which includes information about the blockchain, its members, the data stored therein, etc.

The block data 670 may store transactional information of each transaction that is recorded within the block 650. For example, the transaction data may include one or more of a type of the transaction, a version, a timestamp, a channel ID of the distributed ledger 630, a transaction ID, an epoch, a payload visibility, a chaincode path (deploy tx), a chaincode name, a chaincode version, input (chaincode and functions), a client (creator) identify such as a public key and certificate, a signature of the client, identities of endorsers, endorser signatures, a proposal hash, chaincode events, response status, namespace, a read set (list of key and version read by the transaction, etc.), a write set (list of key and value, etc.), a start key, an end key, a list of keys, a Merkel tree query summary, and the like. The transaction data may be stored for each of the N transactions.

In some embodiments, the block data 670 may also store data 672 which adds additional information to the hash-linked chain of blocks in the blockchain 632. Accordingly, the data 672 can be stored in an immutable log of blocks on the distributed ledger 630. Some of the benefits of storing such data 672 are reflected in the various embodiments disclosed and depicted herein.

The block metadata 680 may store multiple fields of metadata (e.g., as a byte array, etc.). Metadata fields may include signature on block creation, a reference to a last configuration block, a transaction filter identifying valid and invalid transactions within the block, last offset persisted of an ordering service that ordered the block, and the like. The signature, the last configuration block, and the orderer metadata may be added by the ordering service 610. Meanwhile, a committer of the block (such as blockchain node 622) may add validity/invalidity information based on an endorsement policy, verification of read/write sets, and the like. The transaction filter may include a byte array of a size equal to the number of transactions in the block data 670 and a validation code identifying whether a transaction was valid/invalid.

Figure 7:
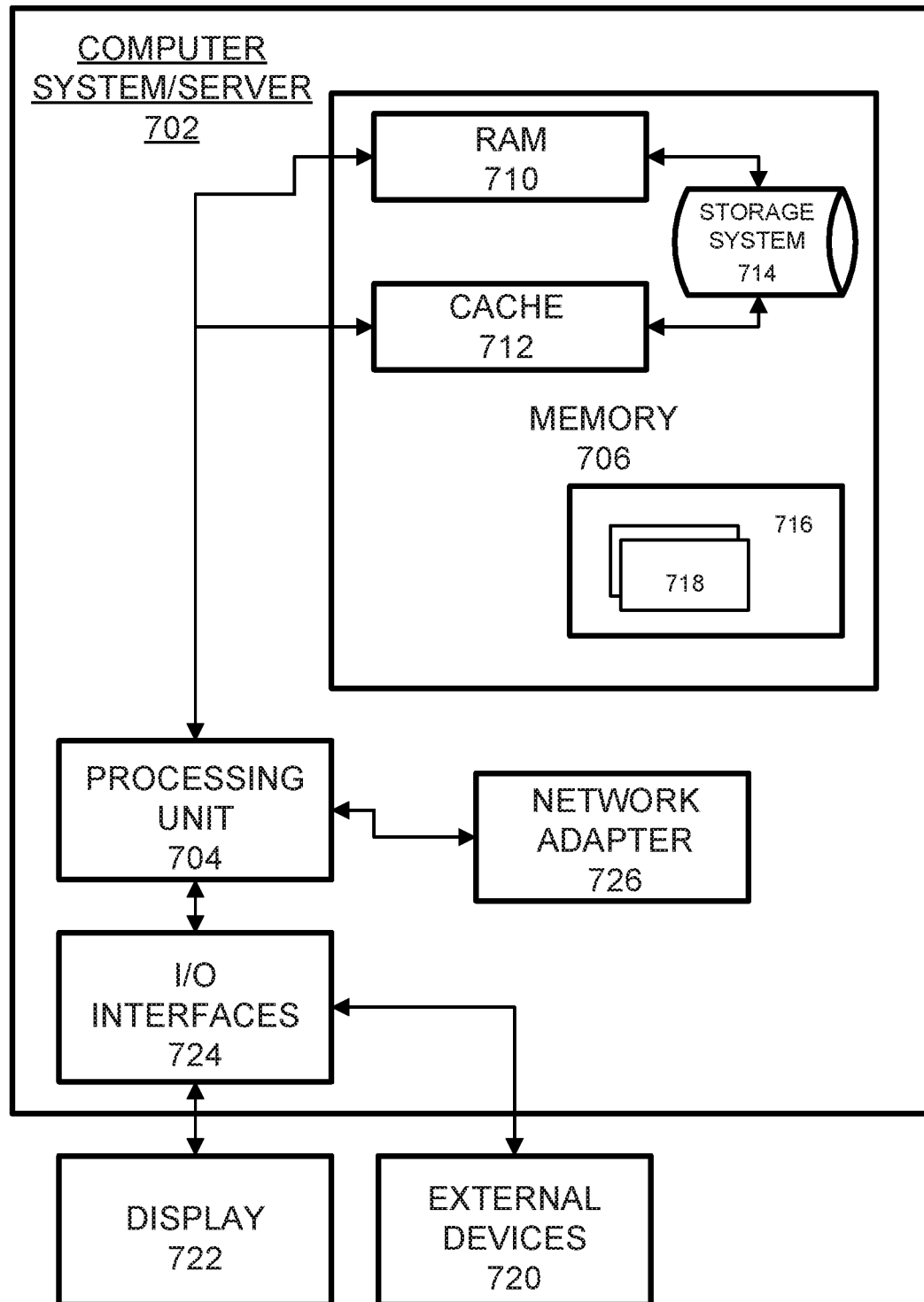
FIG. 7 illustrates an example system that supports one or more of the example embodiments.

FIG. 7 is not intended to suggest any limitation as to the scope of use or functionality of embodiments of the application described herein. Regardless, the computing node 700 is capable of being implemented and/or performing any of the functionality set forth hereinabove.

In computing node 700 there is a computer system/server 702, which is operational with numerous other general purposes or special purpose computing system environments or configurations. Examples of well-known computing systems, environments, and/or configurations that may be suitable for use with computer system/server 702 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 702 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 702 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 7, computer system/server 702 in cloud computing node 700 is shown in the form of a general-purpose computing device. The components of computer system/server 702 may include, but are not limited to, one or more processors or processing units 704, a system memory 706, and a bus that couples various system components including system memory 706 to processor 704.

The bus represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 702 typically includes a variety of computer system readable media. Such media may be any available media that is accessible by computer system/server 702, and it includes both volatile and non-volatile media, removable and non-removable media. System memory 706, in one embodiment, implements the flow diagrams of the other figures. The system memory 706 can include computer system readable media in the form of volatile memory, such as random-access memory (RAM) 710 and/or cache memory 712. Computer system/server 702 may further include other removable/non-removable, volatile/non-volatile computer system storage media. By way of example only, storage system 714 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to the bus by one or more data media interfaces. As will be further depicted and described below, memory 806 may include at least one program product having a set (e.g., at least one) of program modules that are configured to carry out the functions of various embodiments of the application.

Program/utility 716, having a set (at least one) of program modules 718, may be stored in memory 706 by way of example, and not limitation, as well as an operating system, one or more application programs, other program modules, and program data. Each of the operating system, one or more application programs, other program modules, and program data or some combination thereof, may include an implementation of a networking environment. Program modules 718 generally carry out the functions and/or methodologies of various embodiments of the application as described herein.

As will be appreciated by one skilled in the art, aspects of the present application may be embodied as a system, method, or computer program product. Accordingly, aspects of the present application may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present application may take the form of a computer program product embodied in one or more computer readable medium(s) having computer readable program code embodied thereon.

Computer system/server 702 may also communicate with one or more external devices 720 such as a keyboard, a pointing device, a display 722, etc.; one or more devices that enable a user to interact with computer system/server 702; and/or any devices (e.g., network card, modem, etc.) that enable computer system/server 702 to communicate with one or more other computing devices. Such communication can occur via I/O interfaces 724. Still yet, computer system/server 702 can communicate with one or more networks such as a local area network (LAN), a general wide area network (WAN), and/or a public network (e.g., the Internet) via network adapter 726. As depicted, network adapter 726 communicates with the other components of computer system/server 702 via a bus. It should be understood that although not shown, other hardware and/or software components could be used in conjunction with computer system/server 702. Examples include, but are not limited to: microcode, device drivers, redundant processing units, external disk drive arrays, RAID systems, tape drives, and data archival storage systems, etc.

Although an exemplary embodiment of at least one of a system, method, and non-transitory computer readable medium has been illustrated in the accompanied drawings and described in the foregoing detailed description, it will be understood that the application is not limited to the embodiments disclosed, but is capable of numerous rearrangements, modifications, and substitutions as set forth and defined by the following claims. For example, the capabilities of the system of the various figures can be performed by one or more of the modules or components described herein or in a distributed architecture and may include a transmitter, recipient or pair of both. For example, all or part of the functionality performed by the individual modules, may be performed by one or more of these modules. Further, the functionality described herein may be performed at various times and in relation to various events, internal or external to the modules or components. Also, the information sent between various modules can be sent between the modules via at least one of: a data network, the Internet, a voice network, an Internet Protocol network, a wireless device, a wired device and/or via plurality of protocols. Also, the messages sent or received by any of the modules may be sent or received directly and/or via one or more of the other modules.

One skilled in the art will appreciate that a "system" could be embodied as a personal computer, a server, a console, a personal digital assistant (PDA), a cell phone, a tablet computing device, a Smart phone or any other suitable computing device, or combination of devices. Presenting the above-described functions as being performed by a "system" is not intended to limit the scope of the present application in any way but is intended to provide one example of many embodiments. Indeed, methods, systems and apparatuses disclosed herein may be implemented in localized and distributed forms consistent with computing technology.

It should be noted that some of the system features described in this specification have been presented as modules, in order to more particularly emphasize their implementation independence. For example, a module may be implemented as a hardware circuit comprising custom very large-scale integration (VLSI) circuits or gate arrays, off-the-shelf semiconductors such as logic chips, transistors, or other discrete components. A module may also be implemented in programmable hardware devices such as field programmable gate arrays, programmable array logic, programmable logic devices, graphics processing units, or the like.

A module may also be at least partially implemented in software for execution by various types of processors. An identified unit of executable code may, for instance, comprise one or more physical or logical blocks of computer instructions that may, for instance, be organized as an object, procedure, or function. Nevertheless, the executables of an identified module need not be physically located together but may comprise disparate instructions stored in different locations which, when joined logically together, comprise the module and achieve the stated purpose for the module. Further, modules may be stored on a computer-readable medium, which may be, for instance, a hard disk drive, flash device, random access memory (RAM), tape, or any other such medium used to store data.

Indeed, a module of executable code could be a single instruction, or many instructions, and may even be distributed over several different code segments, among different programs, and across several memory devices. Similarly, operational data may be identified and illustrated herein within modules and may be embodied in any suitable form and organized within any suitable type of data structure. The operational data may be collected as a single data set or may be distributed over different locations including over different storage devices, and may exist, at least partially, merely as electronic signals on a system or network.

It will be readily understood that the components of the application, as generally described and illustrated in the figures herein, may be arranged and designed in a wide variety of different configurations. Thus, the detailed description of the embodiments is not intended to limit the scope of the application as claimed but is merely representative of selected embodiments of the application.

One having ordinary skill in the art will readily understand that the above may be practiced with steps in a different order, and/or with hardware elements in configurations that are different than those which are disclosed. Therefore, although the application has been described based upon these preferred embodiments, it would be apparent to those of skill in the art that certain modifications, variations, and alternative constructions would be apparent.

While preferred embodiments of the present application have been described, it is to be understood that the embodiments described are illustrative only and the scope of the application is to be defined solely by the appended claims when considered with a full range of equivalents and modifications (e.g., protocols, hardware devices, software platforms, etc.) thereto.

What is claimed is:

1. A method, comprising:
   receiving, by a pharmacy node in a blockchain network, a request from a patient node for a refill of a prescription, the request containing a secret key of a patient associated with the patient node;
   extracting, by the pharmacy node, the secret key from the request to verify an identify of the patient;
   decrypting, by the pharmacy node, a prescription data of the patient retrieved from a blockchain ledger of the blockchain network using the secret key;
   generating, by the pharmacy node, an authorization to refill the prescription, where the generating an authorization further comprises:
     identifying, by the pharmacy node, a location of origin of the patient from the prescription data,
     identifying, by the pharmacy node, rules for refilling the prescription that are associated with a jurisdiction of origin of the patient based on a smart contract,
     identifying, by the pharmacy node, that the request for the refill originates in a different jurisdiction than the jurisdiction of origin,
     in response to the identification that the request for the refill originates in the different jurisdiction, retrieving a boarding pass from the blockchain ledger and verifying that the patient is travelling to the different jurisdiction from where the request for refill originates based on the retrieved boarding pass, and
     in response to the verification, modifying, by the pharmacy node, the smart contract to implement local rules of the different jurisdiction, wherein the local rules include a listing of medications that cannot be obtained within the different jurisdiction which are different than a listing of medications that cannot be obtained in the jurisdiction of origin,
   determining, by the pharmacy node, that a medication included in the refill is permitted based on the modified smart contract including the listing of medications that cannot be obtained within the different jurisdiction;
   in response to the medication included in the refill not being available, identifying an equivalent medication which is available for the patient in the different jurisdiction based on a prescription equivalence table of the pharmacy node; and
   committing, by the pharmacy node, a transaction to the blockchain ledger based on the determination to permit the refill.

2. The method of claim 1, further comprising:
   updating the blockchain ledger with a number of remaining refills based on the transaction.

3. The method of claim 1, further comprising:
   identifying that the patient will be on a trip having a certain duration based on information stored in the blockchain ledger; and calculating a quantity of medication to be dispensed based on the certain duration.

4. The method of claim 1, further comprising:
calculating an out of pocket cost for the prescription refill based on insurance data of the patient retrieved from the blockchain ledger.

5. The method of claim 1, further comprising:
identifying that a generic substitute exists for the refill from the prescription equivalence table.

6. A non-transitory computer-readable medium configured to store one or more instructions that when executed by a processor of a pharmacy node in a blockchain network configure the processor to perform:
receiving a request for a refill of a prescription from a patient node in the blockchain network, the request containing a secret key of a patient associated with the patient node;
extracting the secret key from the request to verify an identify of the patient; and
decrypting a prescription data of the patient retrieved from a blockchain ledger of the blockchain network using the secret key;
generating an authorization to refill the prescription, where the generating an authorization further comprises:
identifying a location of origin of the patient from the prescription data,
identifying, based on a smart contract, rules for refilling the prescription that are associated with a jurisdiction of origin of the patient,
identifying that the request for the refill originates in a different jurisdiction than the jurisdiction of origin,
in response to the identification that the request for the refill originates in the different jurisdiction, retrieving a boarding pass from the blockchain ledger and verifying that the patient is travelling to the different jurisdiction from where the request for refill originates based on the retrieved boarding pass, and
in response to the verification, modifying the smart contract to implement local rules of the different jurisdiction, wherein the local rules include a listing of medications that cannot be obtained within the different jurisdiction which are different than a listing of medications that cannot be obtained in the jurisdiction of origin,
determining that a medication included in the refill is permitted based on the modified smart contract including the listing of medications that cannot be obtained within the different jurisdiction;
in response to the medication included in the refill not being available, identifying an equivalent medication which is available for the patient in the different jurisdiction based on a prescription equivalence table of the pharmacy node; and
committing a transaction to the blockchain ledger based on the determination to permit the refill.

7. The non-transitory computer readable medium of claim 6, wherein the one or more instructions further cause the processor to perform:
updating the blockchain ledger with a number of remaining refills based on the transaction.

8. The non-transitory computer readable medium of claim 6, wherein the one or more instructions further cause the processor to perform:
identifying that the patient will be on a trip having a certain duration based on information stored in the blockchain ledger; and
calculating a quantity of medication to be dispensed based on the certain duration.

9. The non-transitory computer readable medium of claim 6, wherein the one or more instructions further cause the processor to perform:
calculating an out of pocket cost for the prescription refill based on insurance data of the patient retrieved from the blockchain ledger.

10. A pharmacy node in a blockchain network, the pharmacy node comprising:
a memory storing one or more instructions; and
a processor that when executing the one or more instructions is configured to:
receive a request from a patient node refill of a prescription, the request containing a secret key of a patient associated with the patient node,
extract the secret key from the request to verify an identify of the patient, and generate an authorization to refill the prescription, where the generating an authorization further comprises:
identify a location of origin of the patient from the prescription data,
identify, based on a smart contract, rules for refilling the prescription that are associated with a jurisdiction of origin of the patient,
identify that the request for the refill originates in a different jurisdiction than the jurisdiction of origin,
in response to the identification that the request for the refill originates in the different jurisdiction, retrieve a boarding pass from the blockchain ledger and verify that the patient is travelling to the different jurisdiction from where the request for refill originates based on the retrieved boarding pass, and
in response to the verification, modify the smart contract to implement local rules of the different jurisdiction, wherein the local rules include a listing of medications that cannot be obtained within the different jurisdiction which are different than a listing of medications that cannot be obtained in the jurisdiction of origin,
determine that a medication included in the refill is permitted based on the modified smart contract which including the listing of medications that cannot be obtained within the different jurisdiction;
in response to the medication included in the refill not being available, identify an equivalent medication which is available for the patient in the different jurisdiction based on a prescription equivalence table of the pharmacy node; and
commit a transaction to the blockchain ledger based on the determination to permit the refill.

11. The pharmacy node of claim 10, wherein the processor is further configured to:
update the blockchain ledger with a number of remaining refills based on the transaction.

12. The pharmacy node claim 10, wherein the processor is further configured to: identify that the patient will be on a trip having a certain duration based on information stored in the ledger; and
calculate a quantity of medication to be dispensed based on the certain duration.

13. The pharmacy node of claim 10, wherein the processor is further configured to:
calculate an out of pocket cost for the prescription refill based on insurance data of the patient retrieved from the blockchain ledger.

14. The pharmacy node of claim 10, wherein the processor is further configured to:
   identify that a generic substitute exists for the refill from the prescription equivalence table.

* * * * *